United States Patent [19]

Holland et al.

[11] 4,410,720
[45] Oct. 18, 1983

[54] 16-FLUORO PROSTAGLANDINS

[75] Inventors: George W. Holland, Cedar Grove; Jane L. Jernow, Verona; Perry Rosen, North Caldwell, all of N.J.

[73] Assignee: Hoffmann-La Roche Inc., Nutley, N.J.

[21] Appl. No.: 314,828

[22] Filed: Oct. 26, 1981

Related U.S. Application Data

[60] Continuation of Ser. No. 245,289, Mar. 19, 1981, abandoned, which is a continuation of Ser. No. 132,720, Mar. 24, 1980, abandoned, which is a division of Ser. No. 26,126, Apr. 2, 1979, Pat. No. 4,227,019, which is a division of Ser. No. 780,878, Mar. 24, 1977, abandoned, which is a division of Ser. No. 614,044, Sep. 17, 1975, Pat. No. 4,036,871, which is a division of Ser. No. 480,458, Jun. 18, 1974, Pat. No. 4,052,446, which is a continuation-in-part of Ser. No. 386,117, Aug. 6, 1973, abandoned.

[51] Int. Cl.$^3$ ............................................. C07C 177/00
[52] U.S. Cl. ..................................... 560/121; 260/395; 556/437; 560/53; 560/106; 560/231; 562/463; 562/503; 549/422
[58] Field of Search ...................... 560/121, 231, 106; 562/503, 463; 556/437; 260/345.7 P, 345.8 P, 395

[56] References Cited

U.S. PATENT DOCUMENTS

| | | | |
|---|---|---|---|
| 3,870,710 | 3/1975 | Martel | 542/426 |
| 3,932,446 | 1/1976 | Schaub | 260/340.7 |
| 3,932,479 | 1/1976 | Bernady | 260/448 |
| 3,933,889 | 1/1976 | Magerlin | 560/121 |
| 3,933,898 | 1/1976 | Nelson | 260/473 |
| 3,959,346 | 5/1976 | Schneider | 560/121 |

OTHER PUBLICATIONS

Burger, Medicinal Chemistry, p. 812, (1961).
Ringold et al., J. Am. Chem. Soc., vol. 86, pp. 4510–4512, Oct. 1964.
Hamburg et al., The Journal of Biological Chemistry, vol. 246, pp. 6713–6721, (1971).

*Primary Examiner*—Robert Gerstl
*Attorney, Agent, or Firm*—Jon S. Saxe; George M. Gould; William H. Epstein

[57] ABSTRACT

11-Unsubstituted 16-fluoro-prostaglandin $E_2$ useful as blood pressure lowering agents.

4 Claims, No Drawings

11-SUBSTITUTED PROSTAGLANDINS

CROSS REFERENCE TO RELATED APPLICATIONS

This application is a continuation of U.S. patent application Ser. No. 06/245,289 filed Mar. 19, 1981, now abandoned, which is a continuation of U.S. patent application Ser. No. 06/132,720 filed Mar. 24, 1980, now abandoned, which in turn is a divisional of U.S. patent application Ser. No. 06/026,126 filed Apr. 2, 1979, now U.S. Pat. No. 4,227,019, which in turn is a divisional of U.S. patent application Ser. No. 780,878 filed Mar. 24, 1977, now abandoned, which in turn is a divisional of U.S. patent application Ser. No. 05/614,044 filed Sept. 17, 1975, now U.S. Pat. No. 4,036,871 which in turn is a division of U.S. patent application Ser. No. 05/480,458 filed June 18, 1974, now U.S. Pat. No. 4,052,446, which in turn is a continuation-in-part of U.S. patent application Ser. No. 386,117, Holland, Jernow and Rosen filed Aug. 6, 1973 now abandoned. Also related to this application is U.S. patent application Ser. No. 300,633, Rosen and Kienzle filed Oct. 25, 1972, U.S. patent application Ser. No. 381,322, Rosen and Kienzle filed July 20, 1973 and U.S. patent application Ser. No. 317,589, filed Dec. 22, 1972, Jernow and Rosen.

SUMMARY OF THE INVENTION

In accordance with this invention, a process has been discovered for preparing prostaglandin active compounds of the formula:

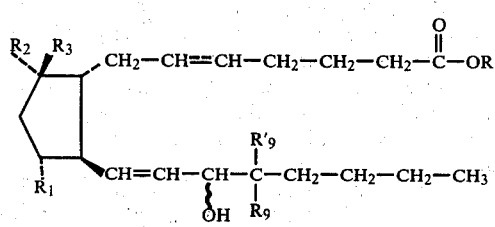

wherein R is hydrogen or lower alkyl; $R_2$ is hydroxy; $R_3$ is hydrogen or taken together with $R_2$ to form oxo; $R_1$ is hydrogen, lower alkyl, carboxy, lower alkoxy carbonyl, $-CH_2OR_8$ and

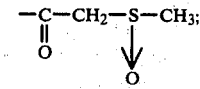

$R_8$ is hydrogen or lower alkyl; $R_9'$ is hydrogen, lower alkyl or fluoro; and $R_9$ is hydrogen or lower alkyl; and the dotted bond can be optionally hydrogenated; from a compound of the formula:

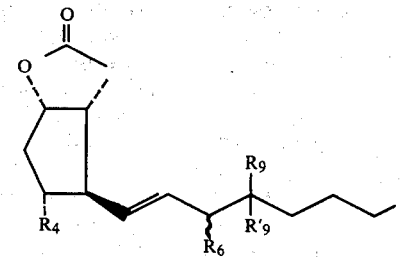

wherein $R_4$ is lower alkyl, hydrogen or $-COOR'_1$; $R_1'$ is hydrogen or lower alkyl; $R_6$ is hydroxy protected with a hydrolyzable ether or ester group; and $R_9$ and $R_9'$ are as above.

In accordance with this invention, new and novel prostaglandin compounds of the formula:

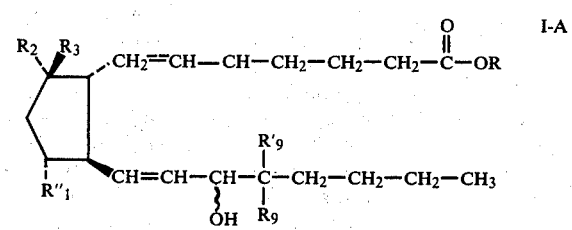

wherein R, $R_2$ and $R_3$ are as above; $R_1''$ is lower alkyl, hydrogen, carboxy, lower alkoxy carbonyl, $-CH_2OR_8$ or

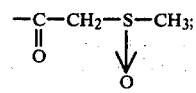

and $R_8$, $R_9$, and $R_9'$ are as above; with the proviso that when $R_9$ and $R_9'$ are all hydrogen, $R_1''$ is lower alkoxycarbonyl, $-CH_2OR_8$ or $$-\underset{\underset{O}{\parallel}}{C}-CH_2-\underset{\downarrow}{S}-CH_3;$$
$$O$$

and the dotted bond can be optionally hydrogenated have been prepared which have cardiovascular activity, induce labor in pregnant females; are useful for terminating pregnancies and for combatting gastro-hyperacidity. The compounds of formula I-A are also useful as bronchodilators.

DETAILED DESCRIPTION OF THE INVENTION

As used throughout this application, the term "lower alkyl" includes both straight chain and branched chain alkyl groups having from 1 to 7 carbon atoms, such as methyl, ethyl and propyl, preferably methyl. As used herein, the term "lower alkoxy" comprehends groups having from 1 to 7 carbon atoms such as methoxy and ethoxy. As also used herein, the term "lower alkanoic acids" comprehends an alkanoic acid of 1 to 7 carbon atoms such as formic acid and acetic acid. As further used herein, the term "halogen" or "halo", unless otherwise stated, comprehends fluorine, chlorine, bromine and iodine.

In the process of this invention, all compounds having one or more asymmetric carbon atoms can be produced as racemic mixtures. These racemic mixtures which are obtained can be resolved at the appropriate steps in the process of this invention by methods well known in the art discussed more fully below, whereupon subsequent products may be obtained as the corresponding optically pure enantiomers.

In the pictorial representation of the compounds given throughout this application, a thickened tapered line ( ▼ ) indicates a substituent which is in the beta-orientation (above the plane of the molecule), a dotted line (---) indicates a substituent which is in the alpha-orientation (below the plane of the molecule) and a wavy line ($\sim\sim\sim$) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aryl lower alkanoic acid" comprehends acids wherein "aryl" and "lower alkanoic acid" are as defined above, particularly benzoic acid.

As still further used herein, the term "carboxy protected with a group convertible thereto by hydrolysis" comprehends any conventional organic acid protecting group which can be removed by hydrolysis. The preferred organic acid protecting groups are the esters. Any conventional ester that can by hydrolyzed to yield the acid can be utilized as the protecting group. Exemplary esters useful for this purpose are the lower alkyl esters, particularly methyl and ethyl ester, the aryl esters, particularly phenyl ester and the aryl lower alkyl esters, particularly benzyl ester.

As used herein, the term "hydrolyzable ester or ether group" designates any ester or ether which can be hydrolyzed to yield the hydroxy group. Exemplary ester groups useful for this purpose are those in which the acyl moiety is derived from a lower alkanoic, an aryl lower alkanoic, phosphoric, carbonic or a lower alkane dicarboxylic acid. Among the acids which can be utilized to form such ester groups are the acid anhydrides and the acid halides, preferably chlorides or bromides, with the lower alkanoic acid anhydrides, e.g., acetic anhydride and caproic anhydride, the aryl lower alkanoic acid anhydrides, e.g., benzoic acid anhydrides, lower alkane dicarboxylic acid anhydrides, e.g., succinic anhydride, and chloroformates, e.g., trichloroethylchloroformate, being preferred. A suitable ether protecting group is, for example, the tetrahydropyranyl ether or 4-methoxy-5,6-dihydro-2H-pyranyl ether. Others are arylmethyl ethers such as benzyl, benzhydryl, or trityl ethers or alpha-lower alkoxy lower alkyl ether, for example, methoxymethyl or allylic ethers, or trialkyl silyl ethers such as trimethyl silyl ether or dimethyl-tert-butyl silyl ethers.

Where $R_1''$ in the compound of formula I-A is $-CH_2OR_8$, the preferred compounds are those where at least one of $R_9$ or $R_9'$ is other than hydrogen. Where $R''_1$ in the compound of formula I-A is lower alkoxycarbonyl, the preferred compounds are those where at least one of $R_9$ or $R_9'$ is other than hydrogen.

The compounds of formula I wherein $R_2$ and $R_3$ form an oxo group, i.e., the compounds of the formula:

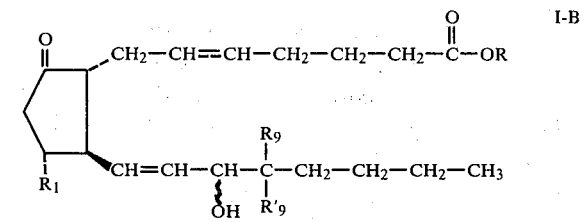

wherein R, $R_1$, $R_9$ and $R_9'$ are as above; and the dotted bond can be optionally hydrogenated; are useful in the same manner as prostaglandin $E_2$. The compounds of formula I-B are especially valuable for preventing hyperacidity in the stomach and for broncho-dilation. On the other hand, the compounds of formula I-A where $R_2$ is hydroxy and $R_3$ is hydrogen, i.e., the compounds of the formula:

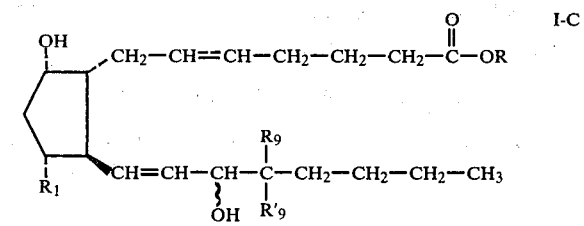

wherein R, $R_1$, $R_9$ and $R_9'$ are as above and the dotted bond can be optionally hydrogenated; are useful in the same manner as prostaglandin $F_{2\alpha}$.

The prostaglandins $E_1$, $E_2$ and $F_{2\alpha}$ have the ability to modify the activity of the alimentary and reproductive smooth muscles to block mucous and enzyme secretions by the stomach, to stimulate the synthesis of adrenal corticoids, to modify blood pressure and lipolysis. Since the compounds of formulae I-B and I-C have prostaglandin $E_1$, $E_2$ and $F_{2\alpha}$ activity, the compounds of formulae I-B and I-C also possess these valuable properties. Furthermore, the compounds of formula I-B and I-C are active in the same manner as these prostaglandins in inducing labor and pregnancy in females and for therapeutically terminating pregnancy. The compounds of formula I-B are useful in the same manner as the prostaglandin $E_2$ in that they lower blood pressure and inhibit blood platelet aggregation. On the other hand, the compounds of formula I-C are blood pressure raising agents in the same manner as prostaglandin $F_{2\alpha}$.

That the compounds of formula I-B are effective anti-ulcerogenic compounds can be seen by the fact that the $ED_{50}$ of a compound such as 7-[3 alpha methyl-5-oxo-2-beta-(3-alpha-hydroxy-4-fluoro-1-trans-octenyl)-1-alphacyclopentyl]-cis-5-heptenoic acid is 0.47 i.p. and 0.0001 p.o. when administered to rats by the following test:

Rats were fasted 16 hours prior to the subcutaneous administration of Indomethacin at 100 mg/kg. Simultaneously with the Indomethacin dose, the test compounds were administered intraperitoneally at three dose levels and dosed orally at six dose levels. These doses of the test compounds were repeated every thirty minutes for six hours (12 doses). After six hours, the animals were killed and the stomachs were examined for ulceration or hemorrhage. Protection from incidence of ulceration was used to determine activity. Five mice were used per dose level and $ED_{50}$ values were calculated.

The compounds of formula I can be used by the pharmaceutical and veterinary arts in a variety of pharmaceutical or veterinary preparations. In these preparations, the new compounds are administerable in the form of tablets, pills, powders, capsules, injectables, solutions, suppositories, emulsions, dispersions, feed pre-mixes and in other suitable forms. The pharmaceutical or veterinary preparations which contain the compound of formula I are conveniently admixed with a non-toxic pharmaceutical organic carrier or a non-toxic pharmaceutical inorganic carrier. Typical of pharmaceutically acceptable carriers are, for example, water, gelatin lactose, starches, magnesium stearate, talc, vegetable oils, polyalkylene glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the compounds will of course vary with the particular novel compounds employed because of the very potency of the compounds, the chosen route of administration and the size of the recipient. The dosage administered is not subject to definite bounds but it will usually be in effective amounts of the pharmacologically function of the prostaglandin. Representative of a typical method for administering the prostaglandin compounds of formula I is by the injectable type administration route. By this route, a sterile solution containing the prostaglandin of formula I can be administered intraveneously at the rate of 0.01 microgram to 0.15 microgram per minute per kilogram of body weight. The compound to be administered by the injectable route is in a form suitable for injection such as mixed with a sterile aqueous solution having incorporated therein an agent that delays adsorption such as aluminum monostereate and the like.

For administering the compounds of formula I to domestic animals or laboratory animals, the compounds are prepared in the form of a food pre-mix such as mixing with dried fish meal, oatmeal and the like, and the prepared pre-mix is added to a regular feed thereby administering the compound to the domestic or laboratory animal in the form of a feed.

The compound of formula I-C wherein $R_1$ is —CH$_2$OR$_8$ and R is hydrogen, i.e., a compound of the formula:

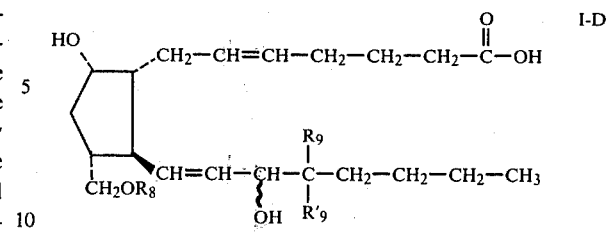

wherein $R_8$, $R_9$ and $R_9'$ are as above; can be prepared from a compound of the formula:

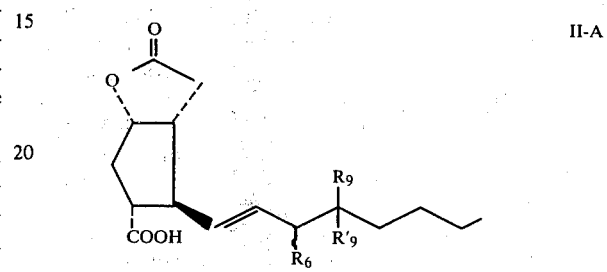

wherein $R_6$, $R_9$ and $R_9'$ are as above; via the following intermediates:

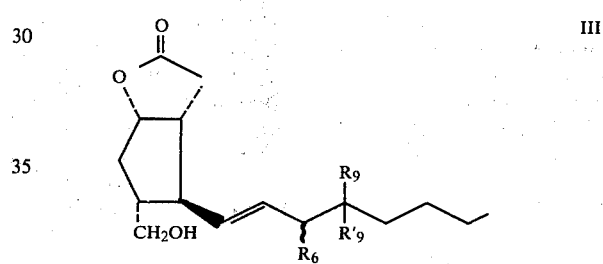

wherein $R_6$, $R_9$ and $R_9'$ are as above;

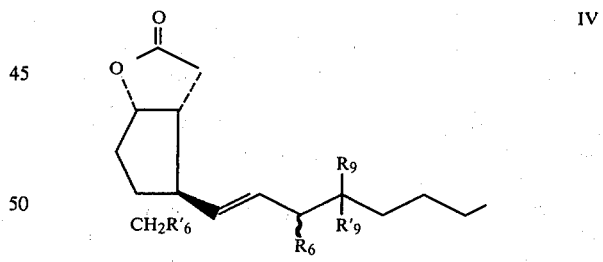

wherein $R_6$, $R_9$ and $R_9'$ are as above; and $R_6'$ is hydroxy protected by a hydrolyzable ether or ester group; or —OR$_8'$ and $R_8'$ is lower alkyl.

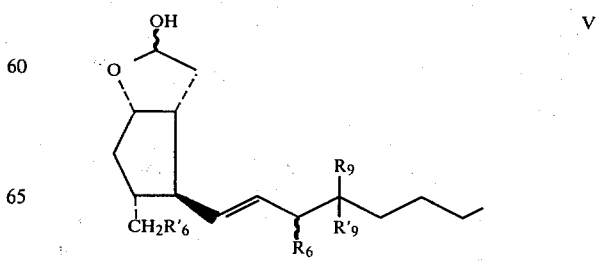

wherein $R_6$, $R_6'$, $R_9'$ are as above;

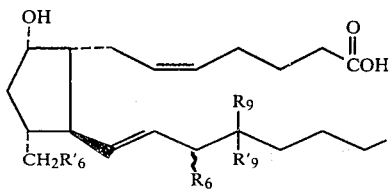

wherein $R_6'$ and $R_6$ are as above.

The starting material of formula II-A when $R_9$ and $R_9'$ are hydrogen and its method of preparation is disclosed in U.S. patent application Ser. No. 300,633, filed Oct. 25, 1972, Kienzle et al. (please note formula XXI-C and Example 20 in Ser. No. 300,633). The compound of formula II-A is converted to the compound of formula III by treating the compound of formula II-A with borane. In carrying out this reaction, temperature and pressure are not critical and the reaction can be carried out at room temperature and atmospheric pressure. On the other hand, elevated or lower temperatures can be utilized. Generally, it is preferred to carry out this reaction at a temperature of from −20° C. to +50° C. This reaction is generally carried out in the presence of an inert organic solvent. In carrying out this reaction, any conventional inert organic solvent can be utilized. Among the preferred solvents are the ether solvents such as diethyl ether, tetrahydrofruan, dioxane, etc.

The compound of formula III is converted to the compound of formula IV by either esterifying or etherifying the free hydroxy group. Any conventional method of etherifying or esterifying the hydroxy group to form a conventional hydrolyzable ether or ester group can be utilized in carrying out this reaction. The preferred protecting group formed by $R_6'$ is tetrahydropyranyloxy. On the other hand, where $R_6'$ is —$OR_8'$ this compound is formed by etherification with a lower alkyl halide. Any of the conditions conventional in forming a lower alkyl ether can be utilized in this conversion.

The compound of formula IV is converted to the compound of formula V by treating the compound of formula IV with a reducing agent. In carrying out this reaction, any conventional reducing agent which will selectively reduce a keto-group to a hydroxy-group can be utilized. Preferred reducing agents are the hydrides, particularly the aluminum hydrides such as alkali metal aluminum hydride, and the borohydrides such as alkali metal borohydrides, with diisobutyl aluminum hydride being particularly preferred. Also, this reaction can be carried out utilizing di-(branched chain lower alkyl)boranes such as bis(3-methyl-2-butyl)borane. In carrying out this reaction, temperature and pressure are not critical and the reaction can be carried out at room temperature and atmospheric pressure or at elevated or reduced temperatures and pressures. Generally, it is preferred to carry out this reaction at a temperature of from −10° C. to the reflux temperature of the reaction mixture. This reduction reaction can be carried out in the presence of an inert organic solvent. Any conventional inert organic solvents can be utilized in carrying out this reaction. Among the preferred solvents are dimethoxy ethylene glycol, and the ethers such as tetrahydrofuran, diethyl ether and dioxane.

The compound of formula VI is obtained from the compound of formula V by reacting the compound of formula V with phosphonium salts of the formula:

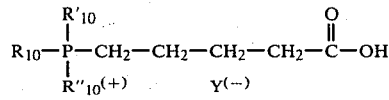

wherein $R_{10}$, $R_{10}'$, $R_{10}''$ is aryl or di(lower alkyl)amino; and Y is halogen.

In accordance with this invention, it is found that the compound of formula V will react with the compound of formula X to produce a compound of the formula VI with a predominately cis double bond at the 5 position of the acid chain in a solvent medium containing hexamethylphosphoramide utilizing sodium bis-trimethylsilylamide as a base. If solvents other than hexamethylphosphoramide or bases other than sodium bis-trimethylsilylamide are utilized, the compound of formula VI will form, if at all, in poor yields. However, conventional inert organic solvents may be mixed with the hexamethylphosphormiade to form the solvent medium in accordance with this invention. If other solvents are utilized, these solvents can be conventional inert organic solvents. On the other hand, the solvent system can contain only the hexamethylphosphoramide. Therefore, this reaction is carried out utilizing hexamethylphosphormiade as the solvent and sodium bis-trimethylsilyl-amide as the base. In carrying out this reaction, temperature and pressure are not critical and this reaction can be carried out at room temperature and pressure. However, if desired, higher or lower temperatures can be utilized. Generally, it is preferred to carry out this reaction at a temperature of from 0° to 50° C.

The process whereby a cis double bond is formed at the 5-position of the heptenoic acid chain can be applied to a process for preparing natural prostaglandins. In this process, a compound of the formula:

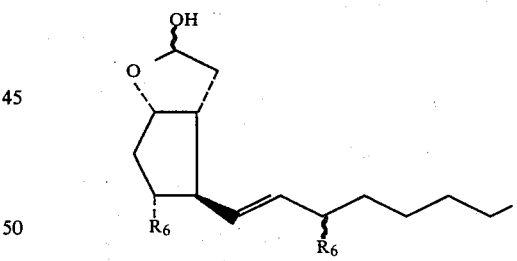

wherein $R_6$ is as above; reacted with a compound of formula X to form a compound of the formula:

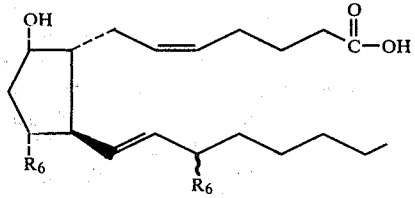

wherein $R_6$ is as above; and where the double bond at the 5-position of the heptenoic acid moiety has a predominately cis configuration. This reaction is carried out in the solvent medium containing hexamethylphosphoramide and in the presence of sodium bis-trimethylsilylamide as the base. The reaction is carried out utilizing the same conditions described in connection with the reaction of a compound of formula V with a compound of formula X to form a compound of formula VI.

The compound of formula VI is converted to the compound of formula I-D by aqueous hydrolysis where the hydroxy group is protected via an ether linkage. Any conventional method of ether hydrolysis can be utilized. Among the preferred methods of ether hydrolysis is by treating the compound of formula VI with an aqueous acid. On the other hand, where $R_6'$ forms $-CH_2OR_8'$, this ether linkage is not a conventional hydrolyzable ether group and conventional ether hydrolysis will not remove the lower alkyl group. On the other hand, where $R_6$ forms an ester linkage, the hydroxy group can be regenerated by treatment with a base in an aqueous medium. Any conventional method of ester hydrolysis can be utilized in this conversion.

On the other hand, the compound of formula VI above can be converted to a compound of the formula:

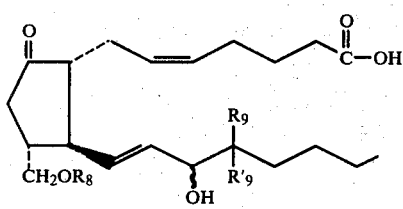

wherein $R_8$, $R_9$ and $R_9'$ are as above; via an intermediate of the formula:

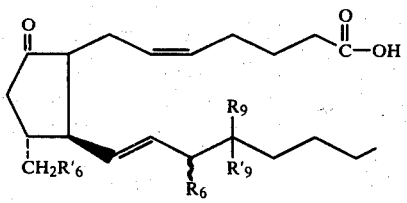

wherein $R_6$, $R_6'$, $R_9$ and $R_9'$ are as above.

The compound of formula VI is converted to a compound of formula VIII by treating the compound of formula VI with an oxidizing agent. Any conventional oxidizing agent which will convert a hydroxy group to an oxo group can be utilized in carrying out this reaction. Among the preferred oxidizing agents are chromate oxidizing agents such as chromium trioxide. Any of the conditions conventional in utilizing these oxidizing agents can be utilized to carry out this reaction. The compound of formula VIII is converted to the compound of formula VII by hydrolysis in the same manner as described in connection with the hydrolysis of a compound of formula VI.

Where $R_1$ in the compound of formula I-C is hydrogen or lower alkyl and R is hydrogen and the double bond is unhydrogenated, this compound has the following formula:

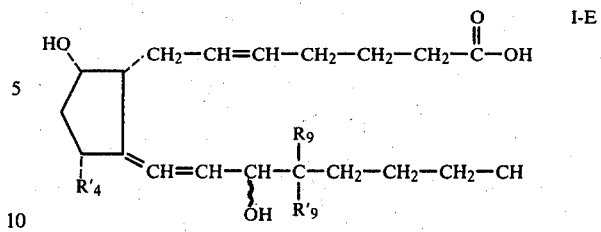

wherein $R_4'$ is lower alkyl or hydrogen, and $R_9$ and $R_9'$ are as above.

This compound can be prepared from a compound of formula II where $R_4$ is hydrogen or lower alkyl via the following intermediates:

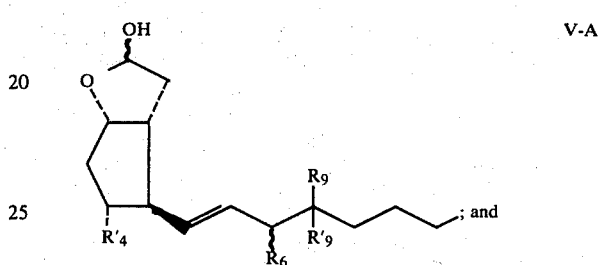

wherein $R_4'$, $R_6$, $R_9$ and $R_9'$ are as above;

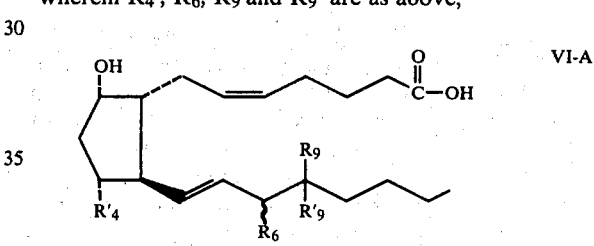

The compound of formula II where $R_4$ is hydrogen or lower alkyl is converted to the compound of formula V-A in the same manner as described in hereinbefore for the conversion of a compound of formula IV to a compound of formula V. The compound of formula V-A is converted to the compound of formula VI-A by reaction with the compound of formula X in the manner described hereinbefore with regard to the conversion of a compound of formula V to a compound of formula VI. The compound of formula VI-A can be converted to a compound of the formula I-E by hydrolysis of the protecting group $R_6$ in the manner described in connection with the conversion of a compound of the formula VI to a compound of the formula I-D.

On the other hand, the compound of formula VI-A can be oxidized to a compound of the formula:

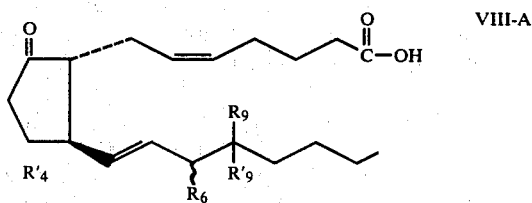

wherein $R_4'$, $R_6$, $R_9$ and $R_9'$ are as above in the same manner as described in connection with the oxidation of a compound of formula VI to a compound of formula VIII. The compound of formula VIII-A can be converted to the compound of the formula:

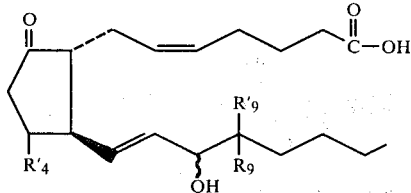

VII-A wherein $R_4'$, $R_9$ and $R_9'$ are as above; by hydrolysis in the manner described in connection with the conversion of the compound of formula VI to a compound of the formula I-D.

The compounds of formula VI, VI-A, VIII and VIII-A can be converted to a compound of the formula:

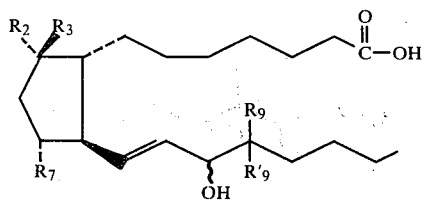

IX wherein $R_2$, $R_3$, $R_9$ and $R_9'$ are as above; and $R_7$ is —$CH_2OR_8$ or lower alkyl or hydrogen, by hydrogenation. Any conventional method of hydrogenation such as catalytic hydrogenation can be utilized to carry out this conversion. Among the preferred methods of hydrogenation is by reacting the compounds of formula VI, VI-A, VIII and VIII-A with hydrogen in the presence of a noble metal catalyst such as platinum or palladium under conditions conventional for such hydrogenation. After hydrogenation, the protecting group can be removed by hydrolysis.

The compounds of formulae I-D, I-E, VII, VII-A and IX can be converted to a compound of the formula:

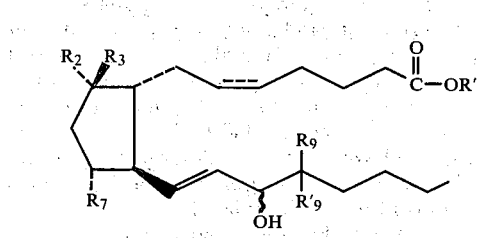

XI wherein $R_2$, $R_3$, $R_7$, $R_9$ and $R_9'$ are as above; R' is lower alkyl; and the dotted bond can be optionally hydrogenated; by esterification with diazomethane or a reactive derivative of a lower alkanol such as a lower alkyl halide. Any conventional conditions utilizing in this esterifying method can be utilized in forming the compound of formula XI from the compounds of formulae I-D, I-E, VII, VII-A or IX. On the other hand, the compound of formula XI can be formed from the compounds of the formulae VI, VI-A, VIII or VIII-A where $R_6$ and $R_6'$ are hydroxy protected with a hydrolozable ether group by esterification as described above to form a compound of the formula:

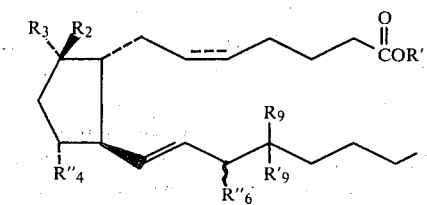

XI-A wherein R', $R_2$, $R_3$, $R_9$ and $R_9'$ are as above; $R_4''$ is hydrogen, lower alkyl, or —$CH_2R_6''$; and $R_6''$ is hydroxy protected with a hydrolozable ether group and the dotted bond can be optimally hydrogenated. The compound of formula XI-A is converted to the compound of formula XI by conventional ether hydrolysis, as described above.

The compound of formula II wherein $R_1'$ is lower alkyl, can be converted to the compound of formula I wherein $R_1$ is:

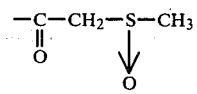

via the following intermediates:

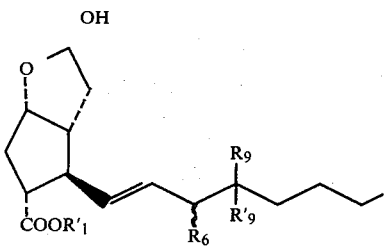

XII wherein $R_1'$, $R_6$, $R_9$ and $R_9'$ are as above;

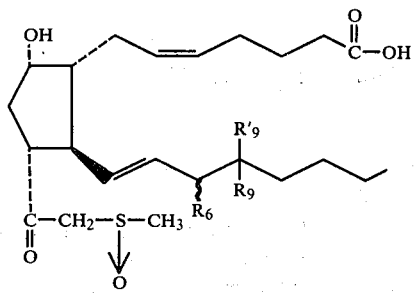

XIII wherein $R_6$, $R_9$ and $R_9'$ are as above.

The compound of formula II wherein $R_4$ is —$COOR_1'$, $R_1'$ is lower alkyl, $R_9$ and $R_9'$ are hydrogen and their methods of preparation are disclosed in Ser. No. 300,633, filed Oct. 25, 1972, Rosen et al. (note compound XXI-C and Example 20 in Ser. No. 300,633, filed Oct. 25, 1972). The compound of formula II where $R_4$ is —$COOR_1$ and $R_1'$ is lower alkyl is converted to the compound of formula XII in the same manner as described above in connection with the conversion of a compound of formula IV to formula V.

The compound of formula XII is converted to the compound of formula XIII by reacting the compound of formula XII with the compound of formula X in the presence of dimethylsulfoxide and an alkali metal hydride base. The dimethylsulfoxide can be utilized as a solvent as well as a reactant in this reaction. On the other hand, any conventional inert organic solvent can be utilized in admixture with dimethylsulfoxide as the organic solvent medium. In carrying out this reaction, alkali methal hydride is utilized as the base. On the other hand, the alkali metal hydride can be combined with dimethylsulfoxide in the form of an alkali metal methyl sulfinylmethylide in this reaction. In carrying out this reaction, temperature and pressure are not critical and this reaction can be carried out at room temperature and atmospheric pressure. On the other hand, higher or lower temperatures can be utilized. Generally, it is preferred to carry out this reaction at a temperature of from $-10°$ C. to $+50°$ C.

The compound of formula XIII is converted to a compound of the formula:

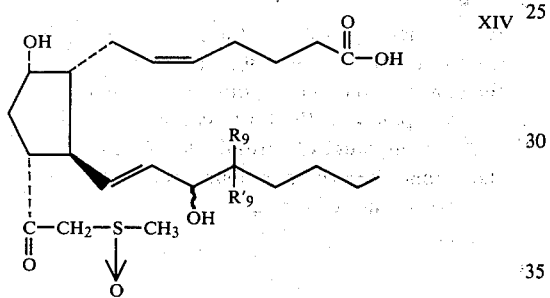

wherein $R_9$ and $R_9'$ are as above; by hydrolysis in the same manner as described in connection with the hydrolysis of a compound of the formula VI.

The compound of formula XIII can be converted to a compound of the formula:

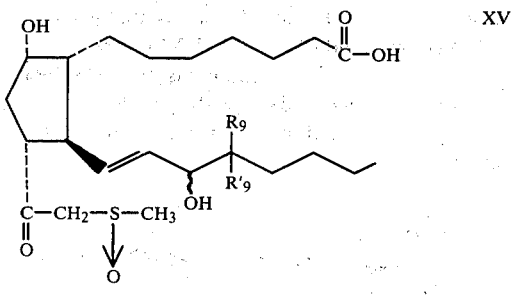

wherein $R_9$ and $R_9'$ are as above; by hydrogenation in the same manner as described in the conversion of compounds of the formulae VI or VIII to a compound of the formula IX above.

The compound of formulae XIV and XV can be converted by esterification with a lower alkanol in the manner described in connection with the esterification of a compound of formulae I-D, VII and IX to form a compound of the formula:

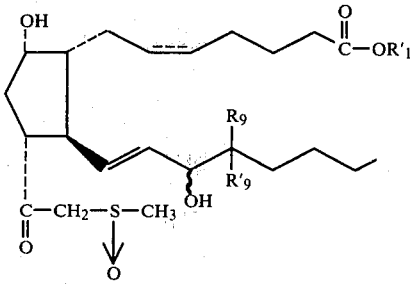

wherein $R_1'$, $R_9$ and $R_9'$ are as above; and the dotted bond can be optionally hydrogenated.

The compound of formula XIII can be converted to a compound of the formula:

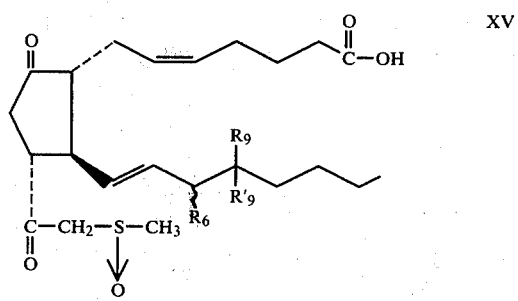

wherein $R_6$, $R_9$ and $R_9'$ are as above; by oxidation in the manner described in connection with the oxidation of a compound of the formula VI to a compound of the formula VII. The compound of formula XV can be hydrolyzed in the manner of the compound of formula VIII and, if desired, hydrogenated, and/or esterified in the manner described above to produce a compound of the formula:

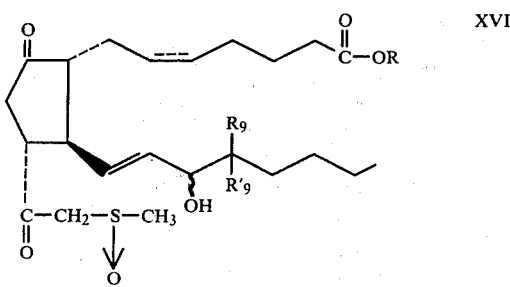

wherein $R_9$, $R_9'$ and R are as above; and the dotted line can be hydrogenated.

Where $R_1$ in the compound of formula I is carboxy or lower alkoxycarbonyl, this compound can be prepared from a compound of formula XII via the following intermediate:

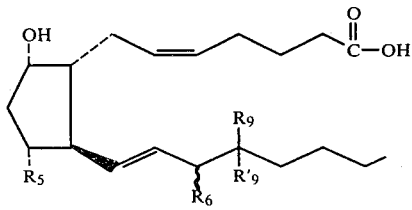

XVII wherein $R_5$ is alkoxycarbonyl or carboxy; and $R_9$, $R_9'$ and $R_6$ are as above. The compound of formula XVII is prepared from the compound of formula XII by reacting the compound of formula XII with a compound of formula X in the same manner as described in connection with the reaction of a compound of the formula V with a compound of formula X.

Where $R_6$ is an esterified hydroxy group in the compound of formula XVII, basic hydrolysis will produce a compound of the formula:

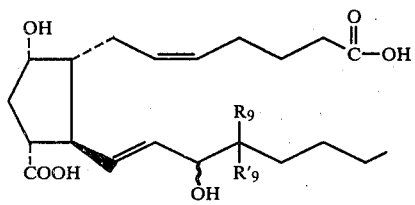

XIX wherein $R_9$ and $R_9'$ are as above. Any conventional means of basic hydrolysis to cleave an ester group can be utilized in carrying out this conversion. On the other hand, $R_6$ in the compound of formula XVII is an etherified hydroxy group, this compound is converted to the compound of the formula:

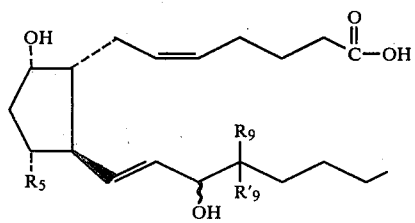

XX wherein $R_9$, $R_9'$ and $R_5$ are as above; by acid hydrolysis. Any conventional method of acid hydrolysis generally used in hydrolyzing ether groups can be utilized in this conversion. The compound of formula XX can, if desired, be converted to a compound of formula XIX by basic hydrolysis in the manner described above.

If desired, the compound of formula XX can be esterified with a lower alkanol or a lower alkyl halide by conventional esterification techniques in the manner described above to produce a compound of the formula:

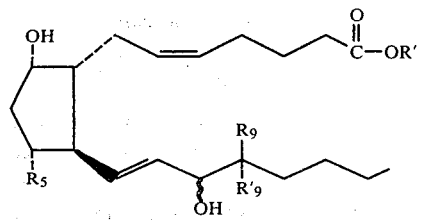

XXI wherein $R_9$, $R_9'$, $R_5$ and $R'$ are as above.

The compound of formula XIX, XX and XXI can be converted to a compound of the formula:

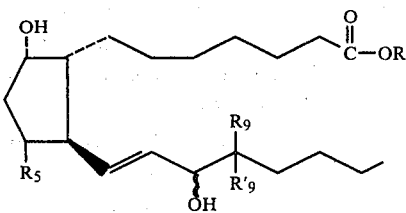

XXII wherein $R_5$, $R_9$, $R_9'$ and R are as above; by hydrogenation in the manner described above in connection with the conversion of a compound of formulae VI and VIII to a compound of the formula IX.

The compound of formula XVII can be oxidized in the manner described in connection with the oxidation of a compound of formula VI to form a compound of the formula:

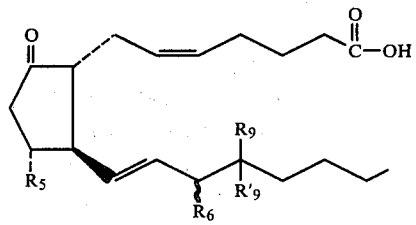

XXIV wherein $R_5$, $R_9$, $R_9'$ and $R_6$ are as above.

The compound of formula XXIV can be hydrolyzed in the manner of the compound of formula XVII and, if desired, esterified and/or hydrogenated in the manner described hereinbefore to form a compound of the formula:

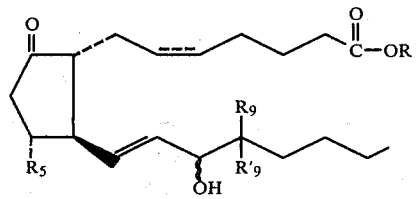

XXVI wherein $R_5$, $R_9$, $R_9'$ and R are as above; and the dotted bond can be optionally hydrogenated.

Where $R_6$ is an ether group, the preferred ether groups are 2-tetrahydropyranyloxy and dimethyl-tert-butylsilyloxy. These ether starting materials of formula II are prepared from compounds of the formula:

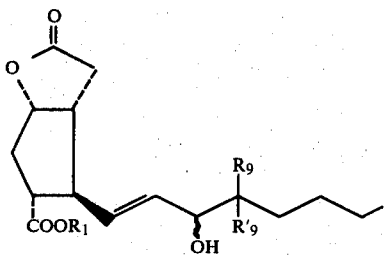

wherein $R_9$ and $R_9'$ are as above. The compounds of formula II-B where $R_9$ and $R_9'$ are hydrogen and their method of preparation are disclosed in U.S. patent application Ser. No. 300,633, filed Oct. 25, 1972, Rosen et al. (Please note compound XXI-C and Example 14 of U.S. patent application Ser. No. 300,633). The compounds of formula II-B are etherified in the conventional manner by reacting with an alcohol or a reactive derivative thereof under conditions conventional in the art.

The compound of formula II can be obtained by first reacting a compound of the formula:

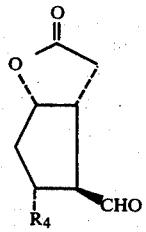

wherein $R_4$ is as above; with either a phosphorane of the formula:

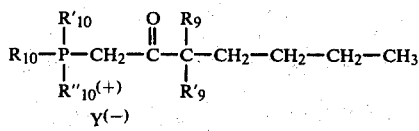

wherein $R_{10}$, $R_{10}'$, $R_{10}''$, $R_9$, $R_9'$ and Y are as above; or a phosphonate of the formula:

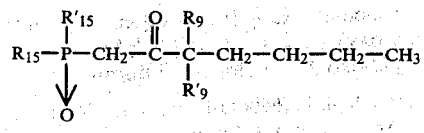

wherein $R_9$ and $R_9'$ are as above; and $R_{15}$ and $R_{15}'$ are aryl, aryloxy or lower alkoxy; to form a compound of the formula:

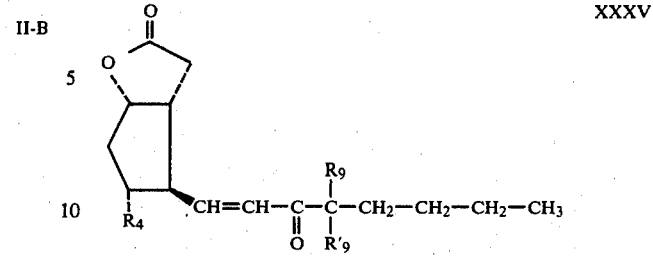

wherein $R_4$, $R_9$ and $R_9'$ are as above; followed by reducing the compound of formula XXXV to form a compound of the formula:

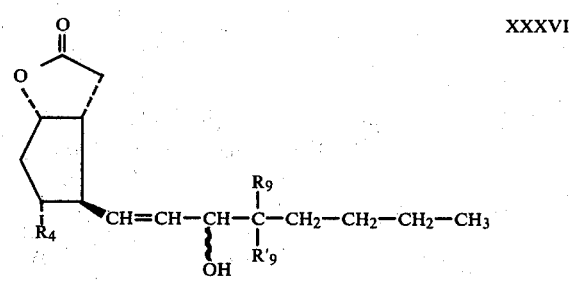

wherein $R_4$, $R_9$ and $R_9'$ are as above; and finally etherifying or esterifying the free hydroxy group.

The reaction of the compound of formula XXVII with the phosphonium salt of formula XXIX to produce a compound of formula XXV is carried out via a Wittig reaction. Any of the conditions conventional in Wittig reactions can be utilized in carrying out this reaction.

The reaction of the compound of formula XXVIII with the phosphonate of formula XXX to produce a compound of formula XXXVI is carried out via a Horner reaction. Any of the conditions conventional in Horner type reactions can be utilized in carrying out this reaction.

The compound of formula XXVIII where $R_4$ is —COOR$_1'$ and its method of preparation is disclosed in U.S. Patent Application Ser. No. 300,633, filed Oct. 25, 1972, Rosen et al. (Please note the compound of formula III and Example 12 of Ser. No. 300,633). The compound fo formula XXVIII where $R_4$ is lower alkyl or hydrogen and its method of preparation is disclosed in U.S. Patent Application Ser. No. 381,322, filed July 20, 1973. (Please note, the compound of formula XVI and Examples 43 and 44 of Ser. No. 381,322). The disclosure of both U.S. Patent Application Ser. No. 300,633 and Ser. No. 381,322 are incorporated by reference.

The compound of formula XXX, where $R_9$ is fluoro, and $R_9'$ is hydrogen or lower alkyl, is prepared by reacting a lithium salt of the formula:

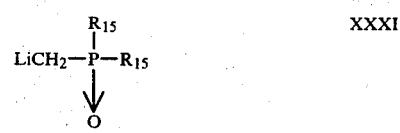

wherein $R_{15}$ is as above; with a compound of the formula:

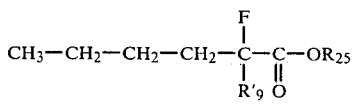
                                                                XXXII wherein $R_{25}$ is lower alkyl, and $R_9'$ is as above. Any of the conditions conventional for reacting a lithium salt with an ester to form an addition product can be used in this reaction.

The compound of formula XXX where $R_9$ is alkyl and $R_9'$ is hydrogen or alkyl can be prepared by reacting the compound of formula XXXI with a compound of the formula:

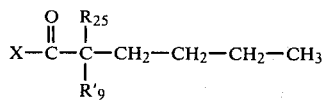
                                                                XXXIII wherein $R_{25}$ is as above and X is a halogen. Any of the conditions conventional in forming addition products by reacting a lithium salt with an acid chloride can be used in carrying out this reaction.

The compound of formula XXIX where $R_9$ and $R_9'$ are not both hydrogen are prepared by reacting a compound of the formula:

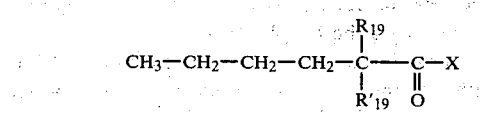

wherein $R_{19}$ is hydrogen, lower alkyl or fluoro; and $R_{19}'$ is lower alkyl or hydrogen with the proviso that at least one of $R_{19}$ and $R_{19}'$ is other than hydrogen; and X is as above; with a compound of the formula:

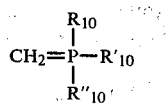

wherein $R_{10}$, $R_{10}'$ and $R_{10}''$ are as above utilizing conventional Wittig conditions.

The compound of formula XXXVI can be obtained by treating the compound of formula XXXV with a reducing agent. In carrying out this reaction, any conventional reducing agent which will selectively reduce a keto-group to a hydroxy group can be utilized. Preferred reducing agents are the hydrides, particularly the aluminum hydrides, such as the alkali metal aluminum hydrides, and the borohydrides, such as the alkali metal borohydrides, with zinc borohydride being quite particularly preferred. In carrying out this reaction, temperature and pressure are not critical, and the reaction can be carried out at room temperature and atmospheric pressure or at elevated or reduced temperatures and pressures. Generally, it is preferred to carry out this reaction at a temperature of from $-10°$ C. to the reflux temperature of the reaction mixture. This reduction reaction can be carried out in the presence of an inert organic solvent. Any conventional inert organic solvent or water can be utilized in carrying out this reaction, such as the conventional, inert organic solvents hereinbefore mentioned. Among the preferred solvents are dimethoxy ethylene glycol and the ethers, such as tetrahydrofuran, diethyl ether and dioxane.

The compound of formula XXXVI may be separated into its two isomers by conventional means to produce one isomer of the formula:

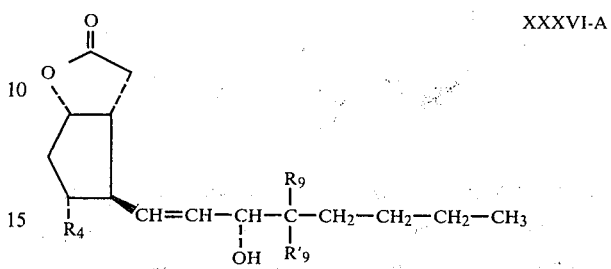
                                                                XXXVI-A and the other isomer of the formula:

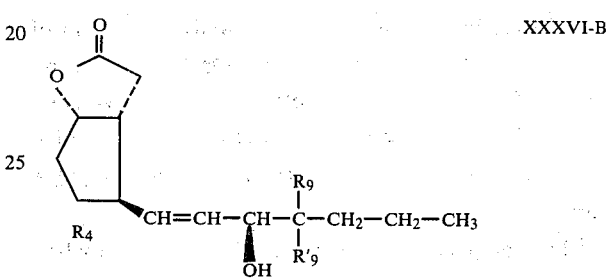
                                                                XXXVI-B wherein $R_4$ is as above. Any conventional means of separation such as column chromatography, vapor phase chromatography, etc., can be utilized to carry out this separation. Either of these isomers can be utilized in accordance with this reaction to produce the compound of formula I. The configuration of the hydroxy group on the octenyl side chain will be carried through the process of this invention so that the hydroxy group on the octenyl side chain in the compound of formula I will have the same configuration as it has in the starting material of formula XXXVI-A or XXXVI-B.

The compound of formulae XXXVI, XXXVI-A and XXXVI-B can be converted to a compound of the formula II by esterifying or etherifying the free hydroxy group with a hydrolyzable ether or ester protecting group. This esterification or etherification can be carried out by conventional esterification or etherification procedures. Among the preferred hydrolyzable ester groups are lower alkanoyloxy with acetoxy being especially preferred. Among the preferred hydrolyzable ether groups are included tetrahydropyranyl.

The following examples are illustrative but not limitative of the invention. All temperatures are in degrees centigrade. The ether utilized in these examples was diethyl ether.

EXAMPLE 1

3,3abeta,4,5,6,6abeta-hexahydro-4beta[3alpha-(2-tetrahydropyranyloxy)-1-trans-octenyl]-5alpha-carbomethoxy-2-oxo-2H-cyclopenta[b]furan 1.90 g. of 3,3abeta,4,5,6,6abeta-hexahydro-4beta-(3alpha-hydroxy-1-trans-octenyl)-2-oxo-2H-cyclopenta[b]furan-5alpha-carboxylic acid methyl ester was mixed with 50 ml. of methylene chloride containing 1.0 ml. of freshly distilled dihydropyran and a trace of p-toluenesulfonic acid. After 30 minutes, the solvent was evaporated and the residual oil purified by column chromatography over silica gel to yield 2.43 g. (100%) 3,3abeta,4,5,6,6abeta-hexahydro-4beta[3alpha-(2-tetrahydropyranyloxy)-1-trans-octenyl]-5alpha-carbomethoxy-2-oxo-2H-cyclopenta[b]furan.

EXAMPLE 2

3,3abeta,4,5,6,6abeta-hexahydro-4beta[3alpha-(2-tetrahydropyranyloxy)-1-trans-octenyl]5alpha-carbomethoxy-2H-cyclopenta[b]furan-2-ol 318 mg. (0.8 mmol) of 3,3abeta,4,5,6,6abeta-hexahydro-4beta[3alpha-(2-tetrahydropyranyloxy)-1-trans-octenyl]-5alpha-carbomethoxy-2-oxo-2H-cyclopenta[b]furan was reacted with a 100% excess of bis-3-methyl-2-butylborane in 25 ml. of tetrahydrofuran at 0° C. under argon for 20 hours. After this period, 5 ml of 3 N aqueous sodium acetate and 1 ml. of 30% by weight aqueous hydrogen peroxide were added and the reaction was allowed to warm to room temperature. After 1 hour, the mixture was cooled to 0° C. and the organic layer separated by addition of anhydrous potassium carbonate. Evaporation of the dried (MgSO₄) organic layer gave 237 mg. (74%) of pure 3,3abeta,4,5,6,6abeta-hexahydro-4beta[3alpha-(2-tetrahydropyranyloxy)-1-trans-octenyl]-5alpha-carbomethoxy-2H-cyclopenta[b]furan-2-ol after column chromatography over silica gel.

EXAMPLE 3

7-{3alpha-carbomethoxy-5-alpha-hydroxy-2beta[3alpha-(2-tetrahydropyranyloxy)-1-trans-octenyl]-1alpha-cyclopentyl}-cis-5-heptenoic acid 414 mg. of 3,3abeta,4,5,6,6abeta-hexahydro-4beta-[3alpha-(2-tetrahydropyranyloxy)-1-trans-octenyl]-5alpha-carbomethoxy-2H-cyclopenta[b]furan-2-ol was reacted under argon in 15 ml. of hexamethylphosphoric triamide with 2.8 equivalents of the Wittig reagent generated from the reaction of sodium bis-trimethylsilyl amide with (4-carboxybutyl)triphenylphosphonium bromide. After one hour, the reaction was neutralized with acetic acid and the solvent removed at 40°-50° C. at high vacuo. Column chromatography of the residual material over silica gel yielded 7-{3alpha-carbomethoxy-5alpha-hydroxy-2beta-[3alpha-(2-tetrahydropyranyloxy)-1-trans-octenyl]-1alpha-cyclopentyl}-cis-5-heptenoic acid.

EXAMPLE 4

3,3abeta,4,5,6,6abeta-hexahydro-4beta(3alpha-dimethyl-tert-butylsilyloxy-1-trans-octenyl)5alpha-carbomethoxy-2-oxo-2H-cyclopenta[b]furan 683 mg. (2.13 mmol) of 3,3abeta,4,5,6,6abeta-hexahydro-4beta-(3alpha-hydroxy-1-trans-octenyl)-2-oxo-2H-cyclopenta[b]furan-5alpha-carboxylic acid methyl ester was mixed with 393 mg. (2.56 mmol) of dimethyl-tert-butylsilyl chloride, 362 mg. (5.33 mmol) of imidazole, and 3 ml. of N,N-dimethylformamide. After 20 hours at 35° C. the reaction mixture was diluted with methylene chloride, washed with water and dried (MgSO₄). Evaporation of the solvent gave 1.01 g. (98%) of 3,3abeta,4,5,6,6abeta-hexahydro-4beta-(3alpha-dimethyl-tert-butylsilyloxy-1-trans-octenyl)-5alpha-carbomethoxy-2-oxo-2H-cyclopenta[b]furan; m.p. 87°-89° C. from hexane.

EXAMPLE 5

3,3abeta,4,5,6,6abeta-hexahydro-4beta(3alpha-dimethyl-tert-butylsilyloxy-1-trans-octenyl)-5alpha-carbomethoxy-2H-cyclopenta[b]furan-2-ol 1.4 g. (3 mmol) of 3,3abeta,4,5,6,6abeta-hexahydro-4beta(3alpha-dimethyl-tert-butylsilyloxy-1-trans-octenyl)-5alpha-carbomethoxy-2-oxo-2H-cyclopenta[b]furan was reacted with 100% excess of bis-3-methyl-2-butyl borane in 50 ml. of tetrahydrofuran under argon at 0° C. After 20 hours, the mixture was oxidized with 6 ml. of 30% by weight aqueous hydrogen peroxide in the presence of 30 ml. of 3 N aqueous sodium acetate. The organic layer was separated by the addition at 10° C. of anhydrous potassium carbonate, dried (MgSO₄) and evaporated to give 1.3 g. (93%) of 3,3abeta,4,5,6,6abeta-hexahydro-4beta-(3alpha-dimethyl-tert-butylsilyloxy-1-trans-octenyl)-5alpha-carbomethoxy-2H-cyclopenta[b]furan-2-ol after purification by column chromatography over silica gel.

EXAMPLE 6

7-[3alpha-carbomethoxy-5alpha-hydroxy-2beta-(3alpha-dimethyl-tert-butylsilyloxy-1-trans-octenyl)-1alpha-cyclopentyl]-cis-5-heptenoic acid 213 mg. of 3,3abeta,4,5,6,6abeta-hexahydro-4beta-(3alpha-dimethyl-tert-butylsilyloxy-1-trans-octenyl)-5alpha-carbomethoxy-2H-cyclopenta[b]furan-2-ol was reacted in 15 ml. of hexamethylphosphoric triamide at 25° C. under argon with 2.8 equivalents of the Wittig reagent generated by the reaction of sodium bis-trimethylsilyl amide with (4-carboxybutyl)-triphenylphosphonium bromide. After one hour, the reaction was poured into 50 ml. of a 1:1 parts by volume mixture of saturated aqueous sodium chloride solution and 30% by weight aqueous phosphoric acid. The resulting mixture was extracted with cyclohexane. Evaporation of the dried (Na₂SO₄) extracts yielded 110 mg. of crude 7-[3alpha-carbomethoxy-5alpha-hydroxy-2beta-(3alpha-dimethyl-tert-butylsilyloxy-1-trans-octenyl)-1alpha-cyclopentyl]-cis-5-heptenoic acid which was purified by column chromatography over silica gel.

EXAMPLE 7

7-[3alpha-carbomethoxy-5alpha-hydroxy-2-beta-(3alpha-hydroxy-1-trans-octenyl)-1alpha-cyclopentyl]-cis-5-heptenoic acid 100 mg. of 7-{3alpha-carbomethoxy-5alpha-hydroxy-2beta-[3alpha-(2-tetrahydropyranyloxy)-1-trans-octenyl]-1-alpha-cyclopentyl}-cis-5-heptenoic acid was heated at 35° C. in 3 ml. of 2:1 parts by volume acetic acid-water for 16 hours. The volatile components were evaporated at 25° C., and 0.5 mmHg, and the crude 7-[3alpha-carbomethoxy-5alpha-hydroxy-2beta-(3alpha-hydroxy-1-trans-octenyl)-1-alpha-cyclopentyl]-cis-5-heptenoic acid purified by column chromatography over silica gel.

EXAMPLE 8

By the procedure of Example 7,7-[3alpha-carbomethoxy-5alpha-hydroxy-2beta-(3alpha-dimethyl-tert-butylsilyloxy-1-trans-octenyl)-1-alpha-cyclopentyl]-cis-5-heptenoic acid was converted to 7-[3alpha-carbomethoxy-5alpha-hydroxy-2beta-(3alpha-hydroxy-1-trans-octenyl)-1alpha-cyclopentyl]-cis-5-heptenoic acid.

EXAMPLE 9

Methyl 7-[3alpha-carbomethoxy-5alpha-hydroxy-2beta-(3alpha-hydroxy-1-trans-octenyl)-1alpha-cyclopentyl]-cis-5-heptenoate 7-[3alpha-carbomethoxy-5alpha-hydroxy-2beta-(3alpha-hydroxy-1-trans-octenyl)-1alpha-cyclopentyl]-cis-5-heptenoic acid was treated with a 50% molar excess of diazomethane in diethyl ether. The solvent was removed with a stream of nitrogen to yield methyl 7-[3alpha-carbomethoxy-5alpha-hydroxy-2beta-(3alpha-hydroxy-1-trans-octenyl)-1alpha-cyclopentyl]-cis-5-heptenoate.

EXAMPLE 10

7-[3alpha-carboxy-5-alpha-hydroxy-2beta-(3alpha-hydroxy-1-trans-octenyl)-1alpha-cyclopentyl]-cis-5-heptenoic acid 100 mg. of 7-[3alpha-carbomethoxy-5-alpha-hydroxy-2beta-(3alpha-hydroxy-1-trans-octenyl)-1alpha-cyclopentyl]-cis-5-heptenoic acid was treated with 2.5 equivalents of lithium hydroxide in 5 ml. of 10:1 parts by volume methanol-water at 25° C. for 6 hours. The mixture was treated with excess Dowex 50W-X8 acid ion exchange resin, filtered, and the solvent evaporated to yield 7-[3alpha-carboxy-5alpha-hydroxy-2beta-(3alpha-hydroxy-1-trans-octenyl)-1alpha-cyclopentyl]-cis-5-heptenoic acid; m.p. 105°-107° C. after purification by column chromatography over silica gel.

EXAMPLE 11

7-[3alpha-(methylsulfinylacetyl)-5alpha-hydroxy-2beta-(3alpha-hydroxy-1-trans-octenyl)-1alpha-cyclopentyl]-cis-5-heptenoic acid 400 mg. of 3,3abeta,4,5,6,6abeta-hexahydro-4beta-[3alpha-(2-tetrahydropyranyloxy)-1-trans-octenyl]-5alpha-carbomethoxy-2H-cyclopenta[b]furan-2-ol was reacted in 15 ml. of dimethylsulfoxide at 25° C. with 2.8 equivalents of the Wittig reagent generated by the reaction of sodium methylsulfinylmethylide with (4-carboxybutyl)-triphenylphosphonium bromide. After 5 hours, the solvent was evaporated at 25° C. (0.1 mmHg.) and the residual paste mixed with 3 ml. of water and 6 ml. acetic acid. This mixture was maintained at 35° C. for 16 hours then the volatile components were removed at 25° C. (0.1 mmHg.). 7-[3alpha-(methylsulfinylacetyl)-5alpha-hydroxy-2beta-(3alpha-hydroxy-1-trans-octenyl)-1alpha-cyclopentyl]-cis-5-heptenoic acid was isolated from the residual material by column chromatography over silica gel.

EXAMPLE 12

Methyl 7-[3alpha-(methylsulfinylacetyl)-5alpha-hydroxy-2beta-(3alpha-hydroxy-1-trans-octenyl)-1 alpha-cyclopentyl]-cis-5-heptenoate 100 mg. of 7-[3alpha-(methylsulfinylacetyl)-5alpha-hydroxy-2beta-(3alpha-hydroxy-1-trans-octenyl)-1-alpha-cyclopentyl]-cis-5-heptenoic acid was dissolved in 1:1 parts by volume methylene chloride ethyl ether and treated with a 50% molar excess of diazomethane. The solvent was removed with a stream of nitrogen to yield methyl 7-[3alpha-methylsulfinylacetyl-5alpha-hydroxy-2beta-(3alpha-hydroxy-1-trans-octenyl)1 alpha-cyclopentyl]-cis-5-heptenoate which was purified by column chromatography over silica gel.

EXAMPLE 13

3,3abeta-4,5,6,6abeta-hexahydro-4beta-[3alpha-(2-tetrahydropyranyloxy)-1-trans-octenyl]-5alpha-hydroxymethyl-2H-cyclopenta[b]furan-2-one To a solution of 0.90 g. (2.36 mmole) of 3,3abeta-4,5,6,6abeta-hexahydro-4beta-[3alpha-(2-tetrahydropyranyloxy)-1-trans-octenyl]-5alpha-carboxy-2H-cyclopenta[b]furan-2-one in 10 ml. of dry tetrahydofuran kept at ice bath temperature was added 20 ml. of a 0.146 molar borane solution in tetrahydrofuran. After stirring at this temperature for one hour and room temperature for 25 minutes, the reaction mixture was decomposed with 5 ml. of water and saturated with sodium chloride. The tetrahydrofuran layer was decanted from the aqueous solution, combined with the ethyl acetate extracts of the aqueous layer, dried (sodium sulfate), and the solvent removed under vacuum leaving 0.80 g. of residue. This material was shown to be homogeneous by tlc analysis and was used directly in the next experiment. Passing the product through a silica gel column yielded an analytical sample of 3,3abeta-4,5,6,6abeta-hexahydro-4beta-[3alpha-(2-tetrahydropyranyloxy)-1-trans-octenyl]-5alpha-hydroxymethyl-2H-cyclopenta[b]furan-2-one.

EXAMPLE 14

3,3abeta,4,5,6,6abeta-hexahydro-4beta-[3alpha-(2-tetrahydropyranyloxy)-1-trans-octenyl]-5alpha-[(2-tetrahydropyranyloxy)methyl]-2H-cyclopenta[b]furan-2-one To a solution of 0.95 g. (2.6 mmol) of 3,3abeta-4,5,6,6-abeta-hexahydro-4beta-[3alpha-(2-tetrahydropyranyloxy)-1-trans-octenyl]-5alpha-hydroxymethyl-2H-cyclopenta[b]furan-2-one in 35 ml. of dry methylene chloride was added 0.35 g. of freshly distilled dihydropyran and 4 mg. of p-toluenesulfonic acid. The mixture was stirred at room temperature for ten minutes and then washed with a 5% by weight aqueous sodium bicarbonate solution. The methylene chloride solution was dried ($Na_2SO_4$) and the solvent and excess dihydropyran removed under vacuum to give 1.144 g. of crude product. An analytical sample of 3,3abeta-4,5,6,6-abeta-hexahydro-4beta-[3alpha-(2-tetrahydropyranyloxy)-1-trans-octenyl]-5-alpha-[(2-tetrahydropyranyloxy)methyl]-2H-cycopenta[b]furan-2-one was obtained by column chromatography.

EXAMPLE 15

3,3abeta-4,5,6,6abeta-hexahydro-4beta-[3alpha-(2-tetrahydropyranyloxy)-1-trans-octenyl]-5alpha-[(2-tetrahydropyranyloxy)methyl]-2H-cyclopenta[b]furan-2-ol Twenty milliliters of toluene were removed by distillation from a solution of 1.144 g. of 3,3abeta,4,5,6,6abeta-hexahydro-4beta-[3-alpha-(2-tetrahydropyranyloxy)-1-trans-octenyl]-5alpha-[(2-tetrahydropyranyloxy)methyl]-2H-cyclopenta[b]furan-2-one in 60 ml. of toluene. To this solution kept under argon and in a Dry Ice-acetone bath was added 3 ml. of a 2.3 molar solution of diisobutyl aluminum hydride in hexane. After stirring for 20 minutes at dry ice temperature, the reaction mixture was decomposed with 3 ml. of methanol and let warm up to room temperature. After the addition of 1 ml. of water and 3 g. of Celite, the reaction mixture was stirred for another 30 minutes, filtered and dried (Na$_2$SO$_4$). The solvent was removed under vacuum to give 1.129 g. of crude product. Chromatography on silica gel of the crude material yielded 0.928 g. of 3,3abeta-4,5,6,6abeta-hexahydro-4beta-[3alpha-(2-tetrahydropyranyloxy)-1-trans-octenyl]-5alpha-[(2-tetrahydropyranyloxy)methyl]-2H-cyclopenta[b]furan-2-ol.

EXAMPLE 16

11-homo-prostaglandin F$_{2\alpha}$,11a,15-bis-(tetrahydropyranyl ether)-preparation in dimethyl sulfoxide To 4 ml. of a 0.6 molar solution of sodium methylsulfinyl carbabion in dimethylsulfoxide was added 0.53 g. (1.2 mmole) of (4-carboxybutyl)triphenylphosphonium bromide in 2 ml. of dry dimethylsulfoxide. To this Wittig reagent was added 0.25 g. (0.5 mmole) of 3,3abeta-4,5,6,6abeta-hexahydro-4beta[3alpha-(2-tetrahydropyranyloxy)-1-trans-octenyl]-5alpha-[(2-tetrahydropyranyloxy)methyl]-2H-cyclopenta[b]furan-2-ol in 10 ml. of dimethylsulfoxide. The reaction mixture was stirred for 30 hours at room temperature, then chilled in an ice bath, and decomposed with 10 ml. of 0.2 N sulfuric acid and followed by 2 ml. of 5% by weight of sodium bicarbonate solution. The solvent was removed in vaccum and residue dissolved in 10 ml. of water. The reaction mixture was adjusted to pH 4 at ice temperature with dilute sulfuric acid and extracted with ethyl acetate three times. The combined extracts were washed with a saturated sodium chloride solution, dried (Na$_2$SO$_4$), and solvent removed. The residue was chromatographed on silica gel to yield a major product, 2alpha-(3-methylsulfinyl-2-hydroxypropyl)-4alpha-[(2-tetrahydropyranyloxy)methyl]-3beta[3alpha-(2-tetrahydropyranyloxy)-1-trans-octenyl]-1-alpha-cyclopentanol and a minor product, 11-homo-prostaglandin F$_{2\alpha}$,1-1a,15-bis(tetrahydropyranyl ether).

EXAMPLE 17

11-Homo-prostaglandin F$_{2\alpha}$,11a,15-bis-(tetrahydropyranyl ether)-preparation in hexamethylphosphoramide To a solution of 666 mg. (1.48 mmole) of (4-carboxybutyl)-triphenylphosphonium bromide in 20 ml. of hexamethylphosphoramide was added 550 mg. (2.96 mmole) of sodium bis-trimethylsilyl amide in 30 ml. of hexmethylphosphoramide. To the above solution was then added 240 mg. (0.53 mmole) of 3,3abeta-4,5,6,6-abeta-hexahydro-4beta-[3alpha-(2-tetrahydropyranyloxy)-1-trans-octenyl]-5alpha-[(2-tetrahydropyranyloxy)methyl]-2H-cyclopenta[b]furan-2-ol in 10 ml. of hexamethylphosphoramide. After stirring at room temperature for 2 hours the reaction mixture was poured into 100 g. of ice-water, acidified to pH 3.5 with dilute sulfuric acid and extracted with cyclohexane (4 times). The cyclohexane extracts were washed with saturated aqueous sodium chloride solution, dried (Na$_2$SO$_4$), and solvent removed to yield 300 mg. of an oil which was chromatographed on silica gel to yield 11-homo-prostaglandin F$_{2\alpha}$,11a,15-bis-(tetrahydropyranyl ether).

EXAMPLE 18

11-Homo-prostaglandin F$_{2\alpha}$

A solution of 200 mg. of 11-homo-prostaglandin F$_{2\alpha}$, 11a-15-bis-(tetrahydropyranyl ether) in 5 ml. of a 3:1 parts by volume acetic acid/water solution was kept at 35° C. for 15 hours. The solvent was then removed under high vacuum and the residue purified via column chromatography to give 11-homo-prostaglandin F$_{2\alpha}$.

EXAMPLE 19

11-Homo-prostaglandin E$_2$,11a,15-bis-(tetrahydropyranyl ether)

To a mixture of 3 g. of chromium trioxide and 4.7 g. of pyridine in 75 ml. of methylene chloride was added at 0° C. 2.2 g. of 11-homo-prostaglandin F$_{2\alpha}$,11a,15-bis (tetrahydropyranyl ether) in 25 ml. of methylene chloride. The mixture was stirred for one hour at room temperature and then filtered through Celite. The Celite was washed with methylene chloride and the combined methylene chloride solution washed with dilute aqueous hydrochloric acid to remove any remaining pyridine. The solvent was then removed under vacuum and the residue purified via column chromatography to give 11-homo-prostaglandin E$_2$,11a,15-bis-(tetrahydropyranyl ether).

EXAMPLE 20

11-Homo-prostaglandin-F$_{1\alpha}$

To a cooled (−20° C.) solution of 0.50 g. of 11-homo-prostaglandin F$_{2\alpha}$, 11a,15-bis (tetrahydropyranyl ether) in 20 ml. of methane was added 150 mg. of a 5% by weight palladium on charcoal catalyst and the mixture hydrogenated under 1 atm. of hydrogen. After 1 mol. of hydrogen was taken up, the mixture was passed through a bed of Celite. After removal of solvent the residue was treated with 3:1 parts by weight acetic acid/water solution for 15 hours at 35° C. The solvent was taken off under high vacuum and the residue purified via column chromatography to give 11-homo-prostaglandin F$_{1\alpha}$.

EXAMPLE 21

Dimethyl(2-oxo-3-fluoro-heptyl)phosphonate

To a solution of 7.7 g. (0.06 mole) of dimethyl methyl-phosphonate in 80 ml. of tetrahydrofuran at −73° C. was added dropwise 43.4 ml. of a 1.42 molar solution of butyl lithium in hexane. After stirring for 5 minutes, a solution of 4 g. (0.03 mole) of ethyl 2-fluorohexanoate in 20 ml. of tetrahydrofuran was added dropwise. The resulting solution was then allowed to warm to 0° and then acidified (pH 3) with 2 N sulfuric acid. The mixture was then extracted with hexane, the hexane solution washed with a saturated sodium chloride solution and then dried (MgSO$_4$). The solvent was then removed under reduced pressure and the residue distilled to give 5.8 g. of dimethyl(2-oxo-3-fluoro-heptyl)phosphonate, b.p. 116°–118°/0.4 mm.

EXAMPLE 22

Dimethyl(3,3-dimethyl-2-oxo-heptyl)phosphonate

A solution of 46.4 g. of dimethyl methyl-phosphonate in 900 ml. of tetrahydrofuran was cooled under argon to −78° (dry ice-acetone bath) and treated dropwise with 220 ml. of 1.54 M n-butyllithium in hexane. After 5 minutes, 27.5 g. of 2,2-dimethylhexanoyl chloride (b.p.

68°–70°/19 mm; prepared from 2,2-dimethylhexanoic acid and excess oxalyl chloride) was added dropwise. The mixture was stirred at −78° for 3 hours, then allowed to warm to 0° over a 30 minute period. The mixture was poured into a separatory funnel containing 50 ml. of water and 2.5 l. of diethyl ether. The layers were separated and the organic layer washed with 4×100 ml. saturated sodium chloride solution, dried (MgSO$_4$) and the ether evaporated at 40°. The residual oil was distilled at reduced pressure to give 37.1 g. of dimethyl (3,3-dimethyl-2-oxo-heptyl)phosphonate; b.p. 97°–103°/0.06 mmHg.

EXAMPLE 23

3,3abeta,4,5,6,6abeta-hexahydro-4beta(4,4-dimethyl-3-oxo-1-trans-octenyl)-5alpha carbomethoxy-2H-cyclopenta[b]furan-2one To a mixture of 3.5 g. of sodium hydride/mineral oil (55% by weight sodium hydride) in 500 ml. of dry dimethoxyethane under argon was added a solution of 20.0 g. of dimethyl(3,3-dimethyl-2-oxo-heptyl)phosphonate in 100 ml. of dimethoxyethane. The mixture was vigorously stirred for 2 hours at room temperature. A solution of 16.0 g. of 3,3abeta-4,5,6,6abeta-hexahydro-4beta-formyl-5alpha carbomethoxy-2-oxo-2H-cyclopenta[b]furan in 120 ml. of dimethoxyethane was added and the mixture stirred for 3 hours at room temperature. After this time, 300 ml. of water was added and the mixture poured into a separatory funnel containing 2 l. of ethyl ether. The layers were separated, and the ether layer was washed with saturated sodium chloride solution, dried (Na$_2$SO$_4$) and the ether evaporated at 40°. The residual oil solidified upon cooling and was recrystallized from diethyl ether/hexane (7:3) to give 23.0 g. of 3,3abeta,4,5,6,6abeta-hexahydro-4beta(4,4-dimethyl-3-oxo-1-trans-octenyl)-5alpha carbomethoxy-2H-cyclopenta[b]furan, m.p. 71°–72°.

EXAMPLE 24

3,3abeta,4,5,6,6abeta-hexahydro-4beta(4,4-dimethyl-3alpha hydroxy-1-trans-octenyl)5alpha carbomethoxy-2H-cyclopenta[b]furan-2-one and 3,3abeta,4,5,6-abeta-hexahydro-4beta(4,4-dimethyl-3beta-hydroxy-1-trans-octenyl)-5alpha carbomethoxy-2H-cyclopenta[b]furan-2-one To a solution of 4.4 g. (13.1 mmol) of 3,3abeta,4,5,6-,6abeta-hexahydro-4beta(4,4-dimethyl-3-oxo-1-trans-octenyl)-5alpha-carbomethoxy-2H-cyclopenta[b]furan-2-one in 100 ml. of 1,2-dimethoxyethane was added a solution of 15 mmol of zinc borohydride in 150 ml. of 1,2-dimethoxyethane. The mixture was stirred for 5 hours then poured into a mixture of 5 ml. of 4 N aqueous sulfuric acid, 100 g. of ice, and 300 ml. of diethyl ether. The layers were separated and the water layer extracted with 2×200 ml. of ether. The combined ether extracts were washed with 3×30 ml. of saturated aqueous sodium chloride solution, dried (Na$_2$SO$_4$) and the solvent evaporated to give colorless oil which upon column chromatography, over silica gel yielded pure 3,3abeta,4,5,6,6abeta-hexahydro-4beta(4,4-dimethyl-3alpha-hydroxy-1-trans-octenyl)-5alpha carbomethoxy-2H-cyclopenta[b]furan-2-one (m.p. 61°–62°) and 3,3abeta,4,5,6,6abeta-hexahydro-4beta(4,4-dimethyl-3beta-hydroxy-1-trans-octenyl)-5alpha carbomethoxy-2H-cyclopenta[b]furan-2-one in approximately equal amounts.

EXAMPLE 25

3,3abeta,4,5,6,6abeta-hexahydro-4beta[4,4-dimethyl-3alpha(2-tetrahydropyranyloxy)-1-trans-octenyl]5alpha carbomethoxy-2H-cyclopenta[b]furan-2-one By the procedure of Example 1, 3,3abeta,4,5,6,6abeta-hexahydro-4beta(4,4-dimethyl-3alpha-hydroxy-1-trans-octenyl)-5alpha-carbomethoxy-2H-cyclopenta[b]furan-2-one was converted to 3,3abeta,4,5,6,6abeta-hexahydro-4beta[4,4-dimethyl-3alpha(2-tetrahydropyranyloxy)-1trans-octenyl]-5alpha-carbomethoxy-2H-cyclopenta[b]furan-2-one.

EXAMPLE 26

3,3abeta,4,5,6,6abeta-hexahydro-4beta[4,4-dimethyl-3alpha(2-tetrahydropyranyloxy)-1-trans-octenyl]-5-alpha carbomethoxy-2H-cyclopenta[b]furan-2-ol By the procedure of Example 2, 3,3abeta,4,5,6,6abeta-hexahydro-4beta[4,4-dimethyl-3alpha(2-tetrahydropyranyloxy)-1-trans-octenyl]-5alpha carbomethoxy-2H-cyclopenta[b]furan-2-one was converted to 3,3abeta,4,5,6,6abeta-hexahydro-4beta[4,4-dimethyl-3alpha(2-tetrahydropyranyloxy)-1-transoctenyl]-5alpha carbomethoxy-2H-cyclopenta[b]furan-2-ol.

EXAMPLE 27

7-{3alpha-carbomethoxy-5alpha-hydroxy-2beta[4,4-dimethyl-3alpha-(2-tetrahydropyranyloxy)-1-trans-octenyl]-1 alpha-cyclopentyl}-cis-5-heptenoic acid By the procedure of Example 3, 3,3abeta,4,5,6,6abeta-hexahydro-4beta[4,4-dimethyl-3alpha(2-tetrahydropyranyloxy)-1-trans-octenyl]-5alpha carbomethoxy-2-H-cyclopenta[b]furan-2-ol was converted to 7-{3-alpha-carbomethoxy-5alpha-hydroxy-2beta[4,4-dimethyl-3alpha(2-tetrahydropyranyloxy)-1-trans-octenyl]-1-alpha-cyclopentyl}-cis-5-heptenoic acid.

EXAMPLE 28

7-[3alpha-carbomethoxy-5alpha-hydroxy-2beta-(4,4-dimethyl-3alpha-hydroxy-1-trans-octenyl)-1alpha-cyclopentyl]-cis-5-heptenoic acid By the procedure of Example 7, 7-{3alpha-carbomethoxy-5alpha-hydroxy-2beta[4,4-dimethyl-3alpha-(2-tetrahydropyranyloxy)-1-trans-octenyl]-1alpha-cyclopentyl}-cis-5-heptenoic acid was converted to 7-[3alpha-carbomethoxy-5-alpha-hydroxy-2beta-(4,4-dimethyl-3alpha-hydroxy-1-trans-octenyl)-1-alpha-cyclopentyl]-cis-5-heptenoic acid.

EXAMPLE 29

7-{3alpha-carbomethoxy-5-oxo-2beta[4,4-dimethyl-3alpha(2-tetrahydropyranyloxy)-1-trans-octenyl]-1 alpha-cyclopentyl]-cis-5-heptenoic acid By the procedure of Example 19, 7-{3alpha-carbomethoxy-5alpha-hydroxy-2beta[4,4-dimethyl-3alpha-(2-tetrahydropyranyloxy)-1-transoctenyl]-1 alpha-cyclopentyl}-cis-5-heptenoic acid was converted to 7-{3alpha-carbomethoxy-5-oxo-2beta[4,4-dimethyl-3alpha-(2-tetrahydropyranyloxy)-1-trans-octenyl]-1 alpha-cyclopentyl}-cis-5-heptenoic acid.

EXAMPLE 30

7-[3alpha-carbomethoxy-5-oxo-2beta(4,4-dimethyl-3alpha-hydroxy-1-trans-octenyl)-1 alpha-cyclopentyl]-cis-5-heptenoic acid By the procedure of Example 7, 7-{3alpha-carbomethoxy-5-oxo-2beta[4,4-dimethyl-3alpha(2-tetrahydropyranyloxy)-1-trans-octenyl]-1 alpha-cyclopentyl}-cis-5-heptenoic acid was converted to 7-[3-alpha-carbomethoxy-5-oxo-2beta(4,4-dimethyl-3alpha-hydroxy-1-trans-octenyl)-1 alpha-cyclopentyl]-cis-5-heptenoic acid.

EXAMPLE 31

3,3abeta,4,5,6,6abeta-hexahydro-4beta(4-fluoro-3-oxo-1-trans-octenyl)-5alpha carbomethoxy-2H-cyclopenta[b]furan-2-one By the procedure of Example 23, 3,3abeta,4,5,6,6abeta-hexahydro-4-beta-formyl-5alpha-carbomethoxy-2-oxo-2H-cyclopenta[b]furan was reacted for 10 hours with dimethyl (2-oxo-3-fluoro-heptyl)phosphonate to produce 3,3abeta,4,5,6,6abeta-hexahydro-4-beta(4-fluoro-3-oxo-1-trans-octenyl)-5alpha-carbomethoxy-2H-cyclopenta[b]furan-2-one.

EXAMPLE 32

3,3abeta,4,5,6,6abeta-hexahydro-4beta(4-fluoro-3alpha-hydroxy-1-trans-octenyl)-5alpha-carbomethoxy-2H-cyclopenta[b]furan-2-one and 3,3abeta,4,5,6,6abeta-hexahydro-4beta(4-fluoro-3beta-hydroxy-1-trans-octenyl)-5alpha-carbomethoxy-2H-cyclopenta[b]furan-2-one By the procedure of Example 24, 3,3abeta,4,5,6,6abeta-hexahydro-4beta(4-fluoro-3-oxo-1-trans-octenyl)-5alpha-carbomethoxy-2H-cyclopenta[b]furan-2-one was reacted with zinc borohydride to form a mixture of 3,3abeta,4,5,6,6abeta-hexahydro-4beta(4-fluoro-3alpha-hydroxy-1-trans-octenyl)-5alpha-carbomethoxy-2H-cyclopenta[b]furan-2-one and 3,3abeta,4,5,6,6abeta-hexahydro-4beta(4-fluoro-3beta-hydroxy-1-trans-octenyl)-5-alpha-cabomethoxy-2H-cyclopenta[b]furan-2-one which was separated by column chromatography over silica gel.

EXAMPLE 33

3,3abeta,4,5,6,abeta-hexahydro-4beta[4-fluoro-3alpha(2-tetrahydropyranyloxy)-1-trans-octenyl]-5alpha-carbomethoxy-2H-cyclopenta[b]furan-2-one By the procedure of Example 1, 3,3abeta,4,5,6,6abeta-hexahydro-4beta (4-fluoro-3alpha-hydroxy-1-trans-octenyl)-5alpha-carbomethoxy-2H-cyclopenta[b]furan-2-one was converted to 3,3abeta,4,5,6,6abeta-hexahydro-4beta[4-fluoro-3alpha(2-tetrahydropyranyloxy)-1-trans-octenyl]-5alpha-carbomethoxy-2H-cyclopenta[b]furan-2-one.

EXAMPLE 34

3,3abeta,4,5,6,6abeta-hexahydro-4beta[4-fluoro-3alpha(2-tetrahydropyranyloxy)-1-trans-octenyl]5-alpha-carbomethoxy-2H-cyclopenta[b]furan-2-ol By the procedure of Example 2, 3,3abeta,4,5,6,6-abeta-hexahydro-4beta [4-fluoro-3alpha-(2-tetrahydropyranyloxy)-1-trans-octenyl]-5alpha-carbomethoxy-2H-cyclopenta[b]furan-2-one was converted to 3,3abeta,4,5,6,6abeta-hexahydro-4beta[4-fluoro-3alpha(2-tetrahydropyranyloxy)-1-trans-octenyl]-5-alpha-carbomethoxy-2H-cyclopenta[b]furan-2-ol.

EXAMPLE 35

7-{3alpha-carbomethoxy-5alpha-hydroxy-2beta-[4-fluoro-3alpha-(2-tetrahydropyranyloxy)-1-trans-octenyl]-1 alpha-cyclopentyl}-cis-5-heptenoic acid By the procedure of Example 3, 3,3abeta,4,5,6,6abeta-hexahydro-4beta[4-fluoro-3alpha-(2-tetrahydropyranyloxy)-1-trans-octenyl]-5alpha-carbomethoxy-2H-cyclopenta[b]furan-2-ol was converted to 7-{3alpha-carbomethoxy-5alpha-hydroxy-2beta-[4-fluoro-3alpha-(2-tetrahydropyranyloxy)-1-trans-octenyl]-1 alpha-cyclopentyl}-cis-5-heptenoic acid.

EXAMPLE 36

7-[3alpha-carbomethoxy-5-alpha-hydroxy-2beta-(4-fluoro-3alpha-hydroxy-1-trans-octenyl)-1 alpha-cyclopentyl]-cis-5-heptenoic acid By the procedure of Example 7, 7-{3alpha-carbomethoxy-5alpha-hydroxy-2beta[4-fluoro-3alpha-(2-tetrahydropyranyloxy)-1-trans-octenyl]-1 alpha-cyclopentyl}-cis-5-heptenoic acid was converted to 7-[3alpha-carbomethoxy-5alpha-hydroxy-2beta-(4-fluoro-3alpha-hydroxy-1-trans-octenyl)-1 alpha-cyclopentyl]-cis-5-heptenoic acid.

EXAMPLE 37

7-{3-alpha-carbomethoxy-5-oxo-2beta[4-fluoro-3alpha-(2tetrahydropyranyloxy)-1-trans-octenyl]-1 alpha-cyclopentyl]-cis-5-heptenoic acid By the procedure of Example 19, 7-{3alpha-carbomethoxy-5alpha-hydroxy-2beta[4-fluoro-3alpha-(2-tetrahydropyranyloxy)-1-trans-octenyl]-1 alpha-cyclopentyl}-cis-5-heptenoic acid was converted to 7-{3alpha-carbomethoxy-5-oxo-2beta[4-fluoro-3alpha-(2-tetrahydropyranyloxy)-1-trans-octenyl]-1 alpha-cyclopentyl}-cis-5-heptenoic acid.

EXAMPLE 38

7-[3alpha-carbomethoxy-5-oxo-2beta(4-fluoro-3alpha-hydroxy-1-trans-octenyl)-1 alpha-cyclopentyl]-cis-5-heptenoic acid By the procedure of Example 7, 7-{3-alpha-carbomethoxy-5-oxo-2beta [4-fluoro-3-alpha-(2-tetrahydropyranyloxy)-1-trans-octenyl]-1 alpha-cyclopentyl]-cis-5-heptenoic acid was converted to 7-[3alpha-carbomethoxy-5-oxo-2beta-(4-fluoro-3alpha-hydroxy-1-trans-octenyl)-1 alpha-cyclopentyl]-cis-5-heptenoic acid.

EXAMPLE 39

11-Homo-prostaglandin $E_2$

By the procedure of Example 18, 200 mg of 11-homo-prostaglandin $E_2$, 11a, 15-bis (tetrahydropyranyl ether) was converted to 11-homo-prostaglandin $E_2$.

EXAMPLE 40

3,3a beta 4,5,6,6a beta-Hexahydro-4-beta[4,4-dimethyl-3-alpha (2-tetrahydropyranyloxy)-1-trans-octenyl]5-alpha carboxy-2H cyclopenta[b]furan-2-one To a solution of 5.95 g. (14.1 mmol) of 3,3a beta, 4,5,6,6a beta-hexahydro-4-beta[4,4-dimethyl-3-alpha (2-tetrahydropyranyloxy)1-trans-octenyl]5 alpha-carbomethoxy-2H-cyclopenta[b]furan-2-one in 50 ml. of methanol was added 5 ml. of 7 N aqueous sodium hydroxide. The mixture was refluxed for five hours, then condensed to a white solid under vacuo. The solid was dissolved in 50 ml. of water, extracted with 50 ml. of ethyl ether, acidified with 4 N aqueous sulfuric acid to pH 1, and saturated with sodium chloride. An oil separated which soon solidified to yield 6.29 g. of white solid (m.p. 147°–150° C.). The solid was dissolved in 400 ml. of 3:7 (v/v) ethyl acetate/benzene and the solution brought to reflux in a Dean-Stark apparatus for 8 hours. Evaporation of the solvent in vacuo and purification by column chromatography over silica gel gave 5.46 g. (95%) of 3,3a beta, 4,5,6,6a-beta-hexahydro-4-beta[4,4-dimethyl-3-alpha (2-tetrahydropyranyloxy)-1-trans-octenyl]5 alpha carboxy-2H-cyclopenta[b]furan-2-one; m.p. 121°–124° C.

EXAMPLE 41

3,3a beta,4,5,6,6a beta-Hexahydro-4-beta[4,4-dimethyl-3 alpha (2-tetrahydropyranyloxy)-1-trans-octenyl]5 alpha-hydroxymethyl-2H-cyclopenta [b]furan-2-one To an ice cooled solution of 7.5 g. (18.4 mmol) of 3,3a beta, 4,5,6,6a beta-hexahydro-4-beta[4,4-dimethyl-3-alpha (2-tetrahydropyranyloxy)-1-trans-octenyl]5 alpha carboxy-2H-cyclopenta[b]furan-2-one in 200 ml of dry tetrahydrofuran under an argon atmosphere, was added 17.6 ml. of 1.14 M borane-tetrahydrofuran complex (20 mmol). After one hour, 50 ml. of methanol was added and the mixture condensed to an oil under vacuo. The oil was taken up in 200 ml. of ethyl ether, washed with 2×10 ml. of saturated aqueous sodium bicarbonate, 10 ml. of saturated aqueous sodium chloride and dried (MgSO$_4$). Evaporation of the solvent in vacuo gave 8.0 g. of oil which upon purification by dry column chromatography over silica gel yielded 6.2 g (85%) of pure 3,3a beta, 4,5,6,6a beta-hexahydro-4-beta[4,4-dimethyl-3 alpha (2-tetrahydropyranyloxy)1-trans-octenyl]5-alpha hydroxy methyl-2H-cyclopenta[b]furan-2-one as a viscous oil.

EXAMPLE 42

3,3a beta,4,5,6,6a beta-Hexahydro-4-beta[4,4-dimethyl 3 alpha (2-tetrahydropyranyloxy)-1-trans-octenyl]5 alpha-[(2-tetrahydropyranyloxy)methyl]-2H-cyclopenta[b]furan-2one By the procedure of Example 1, 3,3a beta,4,5,6,6a beta-hexahydro-4beta[4,4-dimethyl-3alpha (2-tetrahydropyranyloxy)1-trans-octenyl]5-alpha-hydroxymethyl-2H-cyclopenta[b]furan-2-one was reacted with dihydropyran to give 3,3beta,4,5,6,6abeta-hexahydro-4-beta[4,4-dimethyl-3alpha(2-tetrahydropyranyloxy)-1-trans-octenyl]5alpha[(2-tetrahydropyranyloxy)methyl]-2H-cyclopenta[b]furan-2-one as a viscous oil.

EXAMPLE 43

3,3a beta,4,5,6,6a beta-Hexahydro-4-beta[4,4-dimethyl-3 alpha (2-tetrahydropyranyloxy)-1-trans-octenyl]5 alpha[(2-tetrahydropyranyloxy)methyl]-2H-cyclopenta[b]furan-2-ol By the procedure of Example 2, 6.35 g. of 3,3a beta,4,5,6,6a beta-hexahydro-4-beta[4,4-dimethyl-3-alpha (2-tetrahydropyranyloxy)-1-trans-octenyl]5alpha[(2-tetrahydropyranyloxy)methyl]-2H-cyclopenta[b]furan-2-one was reacted with bis (3-methyl-2-butyl)borane to yield after purification 5.73 g. (90%) of 3,3a beta,4,5,6,,6a beta-hexahydro-4-beta[4,4-dimethyl-3 alpha (2-tetrahydropyranyloxy)-1-trans-octenyl]5 alpha[2-tetrahydropyranyloxy)methyl]-2H-cyclopenta[b]furan-2-ol as a viscous oil.

EXAMPLE 44

7-{3alpha-(2-tetrahydropyranyloxy)methyl-5alpha-hydroxy-2beta[4,4-dimethyl-3-alpha(2-tetrahydropyranyloxy)-1-trans-octenyl]-1 alpha-cyclopentyl]cis-5-heptenoic acid To 2.1 equivalents of the Wittig reagent generated by the reaction of sodium bis-trimethylsilyl amide with (4-carboxybutyl)-tri-phenylphosphonium bromide in 300 ml. of hexamethyl phosphoric triamide at 25° C. under argon was added a hexamethylphosphoric triamide solution of 5.67 g. of 3,3abeta,4,5,6,6a beta-hexahydro-4beta[4,4-dimethyl-3alpha (2-tetrahydropyranyloxy)-1-trans-octenyl]5alpha[(2-tetrahydropyranyloxy)methyl]-2H-cyclopenta[b]furan-2-ol. After 30 minutes the excess Wittig reagent was destroyed with glacial acetic acid and the volatile components removed by distillation at 60°–75° C./0.04 mmHg. The residue plus 3.0 g. of sodium hydroxide was dissolved in 250 ml. of water, filtered, and stirred under argon at 25° C. for 36 hours. The solution was acidified to pH 4 1 N aqeous sulfuric acid, saturated with sodium chloride, and extracted with 5×200 ml. of ethyl ether. Evaporation of the ether solvent gave 10.42 g. of material which upon purification by dry column chromatography over silica gel yielded 5.90 g. (87%) of 7-{3alpha-(2-tetrahydropyranyloxy)-methyl-5alpha-hydroxy-2beta[4,4-dimethyl-3alpha-(2-tetrahydropyranyloxy)-1-trans-octenyl]-1-alpha-cyclopentyl}cis-5-heptenoic acid.

EXAMPLE 45

7[3 alpha-hydroxymethyl-5 alpha hydroxy-2 beta (4,4-dimethyl-3 alpha hydroxy-1-trans-octenyl)-1-alpha cyclopentyl]-cis-5-heptenoic acid By the procedure of Example 7, 7-{3 alpha-(2-tetrahydropyranyloxy)methyl-5 alpha-hydroxy-2-beta[4,4-dimethyl-3-alpha (2-tetrahydropyranyloxy)-1-trans-octenyl]-1-alpha-cyclopentyl}cis-5-heptenoic acid was converted to 7-[3 alpha-hydroxymethyl-5 alpha-hydroxy-2-beta(4,4-dimethyl-3 alpha hydroxy-1-trans-octenyl)-1 alpha cyclopentyl]-cis-5-heptenoic acid.

EXAMPLE 46

7-{3 alpha-(2-tetrahydropyranyloxy)methyl-5-oxo-2-beta [4,4-dimethyl-3 alpha (2-tetrahydropyranyloxy)-1-trans-octenyl]-1 alpha-cyclopentyl}-cis-5-heptenoic acid.

By the procedure of Example 19, 7-{3 alpha-(2-tetrahydropyranyloxy)methyl-5-alpha hydroxy-2 beta [4,4-dimethyl-3 alpha (2-tetrahydropyranyloxy)-1-trans-octenyl]-1-alpha-cyclopentyl}-cis-5-heptenoic acid was converted to 7-{3 alpha-(2-tetrahydropyranyloxy)methyl-5-oxo-2 beta [4,4-dimethyl-3 alpha(2-tetrahydropyranyloxy)-1-trans-octenyl]-1-alpha-cyclopentyl}-cis-5-heptenoic acid.

EXAMPLE 47

7-[3 alpha-hydroxymethyl-5-oxo-2 beta (4,4-dimethyl-3 alpha hydroxy-1-trans-octenyl)-1 alpha cyclopentyl]-cis-5-heptenoic acid A mixture of 980 mg. of 7-{3 alpha-(2-tetrahydropyranyloxy) methyl-5-oxo-2 beta [4,4-dimethyl-3 alpha (2-tetrahydropyranyloxy)-1-trans-octenyl]-1 alpha cyclopentyl}-cis-5-heptenoic acid and 90 ml. of 1:2 (v/v) glacial acetic acid water was agitated at 25° C. for 120 hours. The volatile components were removed at 35°–40° C./0.5 mmHg and the residue purified by column chromatography over silica gel to yield 366 mg. (53%) of 7-[3 alpha-hydroxymethyl-5-oxo-2 beta (4,4-dimethyl-3-alpha hydroxy-1-trans-octenyl)-1 alpha cyclopentyl]-cis-5-heptenoic acid as a viscous oil.

EXAMPLE 48

Methyl 7-[3 alpha hydroxymethyl-5 alpha hydroxy-2 beta (4,4-dimethyl-3 alpha hydroxy-1-trans octenyl)-1 alpha cyclopentyl]-cis-5-heptenoate An etheral solution of 7-[3 alpha hydroxymethyl-5 alpha hydroxy-2 beta (4,4-dimethyl-3 alpha hydroxy-1-trans octenyl)-1 alpha cyclopentyl] cis-5-heptenoic acid was treated with a solution of diazomethane in diethyl ether until the yellow color persisted for more than 10 minutes. Evaporation of the solvent gave methyl 7-[3 alpha hydroxymethyl-5 alpha hydroxy-2 beta (4,4-dimethyl-3-alpha hydroxy-1-trans octenyl)-1 alpha cyclopentyl]-cis-5-heptenoate.

EXAMPLE 49

Methyl 7-[3 alpha hydroxymethyl-5-oxo-2 beta (4,4-dimethyl 3 alpha hydroxy-1-trans-octenyl)-1 alpha cyclopentyl]-cis-5-heptenoate By the procedure of Example 48, 7-[3 alpha hydroxymethyl-5-oxo-2 beta (4,4-dimethyl-3-alpha hydroxy-1-trans-octenyl)-1 alpha cyclopentyl]-cis-5-heptenoic acid was converted into methyl 7-[3 alpha hydroxymethyl-5-oxo-2 beta (4,4-dimethyl-3 alpha hydroxy-1-trans-octenyl)-1 alpha cyclopentyl]-cis-5-heptenoate. m.p.=51°–52° C.

EXAMPLE 50

Methyl 7-{3 alpha-(2-tetrahydropyranyloxy)methyl-5 alpha hydroxy 2 beta [4,4-dimethyl-3 alpha (2-tetrahydropyranyloxy)-1-trans ocetenyl]-1 alpha cyclopentyl} cis-5-heptenoate By the procedure of Example 48, 7-[3 alpha-(2-tetrahydropyranyloxy)methyl-5 alpha hydroxy 2 beta [4,4-dimethyl-3 alpha (2-tetrahydropyranyloxy)-1-trans octenyl]-1 alpha cyclopentyl} cis-5-heptenoic acid was converted into methyl 7-{3 alpha-(2-tetrahydropyranyloxy) methyl-5 alpha hydroxy-2-beta [4,4-dimethyl-3-alpha(2-tetrahydropyranyloxy)-1-trans octenyl]-1 alpha cyclopentyl} cis-5-heptenoate.

EXAMPLE 51

Methyl 7-{3 alpha-(2-tetrahydropyranyloxy)methyl-5 oxo-2 beta [4,4-dimethyl-3 alpha (2-tetrahydropyranyloxy)-1-trans octenyl]-1 alpha-cyclopentyl} cis-5-heptenoate By the procedure of Example 19, methyl 7-{3 alpha-(2-tetrahydropyranyloxy)methyl-5 alpha hydroxy-2 beta [4,4-dimethyl-3 alpha (2-tetrahydropyranyloxy)-1-trans-octenyl]-1alpha cyclopentyl} cis-5-heptenoate was converted into methyl 7-{3 alpha-(2-tetrahydropyranyloxy) methyl-5-oxo-2 beta [4,4-dimethyl-3 alpha (2-tetrahydropyranyloxy)-1-trans-octenyl]-1-alpha cyclopenyl} cis-5-heptenoate.

EXAMPLE 52

By the procedure of Example 47, methyl 7-{3 alpha-(2-tetrahydropyranyloxy)methyl-5-oxo-2 beta [4,4-dimethyl-3-alpha (2-tetrahydropyranyloxy)-1-trans octenyl]-1 alpha-cyclopentyl}cis-5-heptenoate is converted to methyl 7-{3 alpha-hydroxymethyl-5 alpha oxo-2 beta [4,4-dimethyl-3 alpha-hydroxy-1-trans-octenyl]-1 alpha cyclopentyl} cis-5-heptenoate.

EXAMPLE 53

11-homo-prostaglandin F$_{2\alpha}$, 11 a, 15-bis (2-tetrahydropyranyl ether) methyl ester By the procedure of Example 48, 11-homo-prostaglandin F$_{2\alpha}$, 11a, 15-bis-(2-tetrahydropyranyl ether) was converted to 11-homo prostaglandin F$_{2\alpha}$, 11a, 15-bis(2-tetrahydropyranyl ether) methyl ester.

EXAMPLE 54

11-homo-prostaglandin E$_2$, 11a, 15-bis-(2-tetrahydropyranyl ether) methyl ester By the procedure of Example 19, 11-homo-prostaglandin F$_{2\alpha}$, 11a, 15-bis (2-tetrahydropyranyl ether) methyl ester was converted to 11-homo-prostaglandin E$_2$ 11a, 15-bis-(2-tetrahydropyranyl ether) methyl ester.

EXAMPLE 55

11-homo-prostaglandin F$_{2\alpha}$ methyl ester

By the procedure of Example 18, 11-homo-prostaglandin F$_{2\alpha}$11a, 15-bis(2-tetrahydropyranyl ether) methyl ester was hydrolyzed to 11-homo-prostaglandin F$_{2\alpha}$ methyl ester.

EXAMPLE 56

11-homo-prostaglandin E$_2$ methyl ester

By the procedure of Example 18, 11-homo-prostaglandin E$_2$ 11a, 15-bis (2-tetrahydropyranyl ether) methyl ester was converted to 11-homo-prostaglandin E$_2$ methyl ester.

EXAMPLE 57

By the procedure of Example 21, lithium dimethyl methyl phosphonate was reacted with 2-methyl-2-fluoroethyl hexanoate to produce dimethyl (-2-oxo-3-methyl-3-fluoroheptyl)-phosphonate b.p. 106° C./0.2 mmHg.

EXAMPLE 58

To a suspension of 0.72 g. of sodium hydride in 150 ml. of dry glyme was added 6 g. of dimethyl (2-oxo-3-fluoroheptyl) phosphonate. After stirring for 1.5 hour, 5 g. of 3,3abeta-4,5,6,6abeta-hexahydro-4beta-formyl-5alpha-methyl-2-oxo-2H-cyclopenta [b] furan dissolved in 30 ml. of glyme was added dropwise at 0° C. After stirring for 3 hours at room temperature, 500 ml. of diethyl ether was added and the mixture was washed with water. The organic layer was then dried (MgSO$_4$) and the solvent removed under reduced pressure. The residue was then washed through 75 g. of silica gel to give 7.1 g. of 3,3abeta-4,5,6,6abeta-hexahydro-4beta-(3-oxo-4-fluoro-1-trans-octenyl)-5alpha-methyl-2-oxo-2H-cyclopenta [b] furan.

EXAMPLE 59

By the procedure of Example 58, 3,3abeta-4,5,6,6abeta-hexahydro-4beta-formyl-5alpha-methyl-2-oxo-2H-cyclopenta [b] furan was reacted with dimethyl (2-oxo-3-methyl-3-fluoroheptyl) phosphonate to give 3,3abeta,4,5,6,6abeta-hexahydro-4beta (3-oxo-4-methyl-4-fluoro-1-trans-octenyl) 5 alpha-methyl-2-oxo-2H-cyclopenta [b] furan.

EXAMPLE 60

By the procedure of Example 58, 3,3abeta 4,5,6,6abeta-hexahydro-4beta-formyl-5alpha-methyl-2-oxo-2H-cyclopenta [b] furan was reacted with dimethyl-(2-oxo-3,3-dimethyl heptyl) phosphonate to give 3,3abeta,4,5,6,6abeta-hexahydro-4-beta(3-oxo-4,4-dimethyl-1-trans-octenyl) 5alpha-methyl-2-oxo-2H-cyclopenta [b] furan.

EXAMPLE 61

To a solution of 4.5 g. of 3,3abeta-4,5,6,6abeta-hexahydro-4beta-(3-oxo-4-fluoro-1-trans-octenyl)-5alpha-methyl-2-oxo-2H-cyclopenta [b] furan in 100 ml. of dry glyme was added an excess of zinc borohydride in 50 ml. of glyme and the resulting solution stirred for 3 hours. The solution was cooled to 0° C. and treated with 200 ml. of water, 400 ml. of ether and 10 ml. of 0.5 N aqueous sulfuric acid. The ether was separated and dried (MgSO$_4$) and the solvent removed under reduced pressure to give 3,3abeta-4,5,6,6a beta-hexahydro-4beta-(3-hydroxy-4-fluoro-1-trans-octenyl)-5alpha-methyl-2-oxo-2H-cyclopenta [b] furan. Column chromatography on silica gel utilizing diethyl ether hexane (70:30 parts by volume) then afforded first the 3,3abeta-4,5,6,6abeta-hexahydro-4beta-(3alpha-hydroxy-4-fluoro-1-trans-octenyl)-5alphamethyl-2-oxo-2H-cyclopenta[b]furan and then 3,3abeta-4,5,6,6abeta-hexahydro-4beta-(3beta-hydroxy-4-fluoro-1-trans-octenyl)-5 alpha-methyl-2-oxo-2H-cyclopenta [b] furan.

EXAMPLE 62

By the procedure of Example 61, 3,3abeta-4,5,6,6abeta-hexahydro-4alpha-(3-oxo-4-fluoro-4-methyl-1-trans-octenyl)-5alpha methyl-2-oxo-2H-cyclopenta [b] furan was converted to 3,3abeta-4,5,6, 6abeta-hexahydro-4beta(3alpha-hydroxy-4-fluoro-4-methyl-1-trans-octenyl)-5alpha methyl-2-oxo-2H-cyclopenta [b] furan and 3,3abeta, 4,5,6,6abeta-hexahydro-4 beta (3 beta-hydroxy-4-fluoro-4-methyl-1-trans-octenyl)-3 alpha methyl-2-oxo-2H-cyclopenta[b]furan which were separated by column chromatography in the manner of Example 61.

EXAMPLE 63

By the procedure of Example 61, 3,3abeta,4,5,6,-,6abeta-hexahydro-4-beta-(3-oxo-4,4-dimethyl-1-trans-octenyl)-5alpha-methyl-2-oxo-2H-cyclopenta[b]furan was converted to 3,3abeta,4,5,6,6abeta hexahydro-4-beta(3alpha-hydroxy-4,4-dimethyl-1-trans-octenyl)-5alpha-methyl-2-oxo-2H-cyclopenta[b]furan and 3,3abeta,5,5,6,6abeta-hexahydro-4-beta (3 beta-hydroxy-4,4-dimethyl-1-trans-octenyl)-5 alpha methyl-2-oxo-2H-cyclopenta[b]furan which was separated by column chromatography in the manner of Example 61.

EXAMPLE 64

A solution of 5 g. of 3,3abeta-4,5,6,6abeta-hexahydro-4-beta-(3alpha-hydroxy-4-fluoro-1-trans-octenyl)-5alpha-methyl-2-oxo-2H-cyclopenta[b]furan. 12 g. of dihydropyran and 25 mg. of p-toluene sulfonic acid in 200 ml. of methylene chloride was stirred at 25° C. for 3 hours. The solution was washed with saturated sodium bicarbonate solution, the methylene chloride solution dried (MgSO$_4$) and the volatile components evaporated under reduced pressure to give 6.4 g. of 3,3abeta-4,5,6,6abeta-hexahydro-4beta [3alpha(2-tetrahydropyranyloxy)-4-fluoro-1-trans-octenyl]5 alpha-methyl-2-oxo-2H-cyclopent[b]furan.

EXAMPLE 65

By the procedure of Example 64, 3,3abeta-4,5,6,6abeta-hexahydro-4-beta-(3alpha-hydroxy-4-fluoro-4-methyl-1-trans-octenyl)-5alpha methyl-2-oxo-2H-cyclopenta[b]furan was converted to 3,3abeta,4,5,6-,6abeta-hexahydro-4beta[3-alpha-(2-tetrahydropyranyloxy)-4-fluoro-4-methyl-1-trans-octenyl]-5-alpha methyl-2-oxo-2H-cyclopenta[b]furan.

EXAMPLE 66

By the procedure of Example 64, 3, 3abeta,4,5,6-,6abeta-hexahydro-4beta-(3alpha-hydroxy-4,4-dimethyl-1-trans-octenyl) 5 alpha-methyl-2H-cyclopenta[b]furan is converted to 3,3abeta,4,5,6,6abeta-hexahydro-4beta-[3alpha(2-tetrahydropyranyloxy)-4,4-dimethyl-1-trans-octenyl]-5alpha-methyl-2H-cyclopenta[b]furan.

EXAMPLE 67

To a solution of 5.3 g. of 3,3abeta-4,5,6,6abeta-hexahydro-4beta-[3alpha(2 tetrahydropyranyloxy)-4-fluoro-1-trans-octenyl]5alpha-methyl-2-oxo-2H-cyclopenta[b]furan in 150 ml. of toluene, was added dropwise at −78° C., 1 equivalent of diisobutylaluminum hydride in the same solvent. The reaction mixture was stirred at this temperature for 2 hours after which time 20 ml. of methanol was slowly added and the mixture stirred for 2 hours at room temperature. The mixture was then filtered thru a bed of charcoal, the charcoal was washed with ethyl acetate and the solvents were then removed under reduced pressure. The residue was then washed thru a column of silica gel to give 3,3abeta-4,5,6,6abeta-hexahydro-4beta[3 alpha(2-tetrahydropyranyloxy)-4-fluoro-1-trans-octenyl]5alpha-methyl-2H-cyclopenta[b]furan-2-ol.

EXAMPLE 68

By the procedure of Example 67, 3,3abeta-4,5,6,6abeta-hexahydro-4beta-[3alpha(2-tetrahydropyranyloxy)-4-fluoro-4-methyl-1-trans-octenyl]-5alpha-methyl-2-oxo-2H-cyclopenta[b]furan was converted to 3,3abeta-4,5,6,6abeta-hexahydro-4beta[3 alpha(2-tetrahydropyranyloxy)-4-fluoro-4-methyl-1-trans-octenyl]-5-alpha-methyl-2H-cyclopenta[b]furan-2-ol.

EXAMPLE 69

By the procedure of Example 67, 3,3abeta-4,5,6,6abeta-hexahydro-4beta[3 alpha (2-tetrahydropyranyloxy)-4,4-dimethyl-1-trans-octenyl]-5 alpha methyl-2-oxo-2H-cyclopenta[b]furan was converted to 3,3abeta-4,5,6,6abeta-hexahydro-4beta[3 alpha (2-tetrahydropyranyloxy)-4,4-dimethyl-1-trans-octenyl]-5-alpha methyl-2H-cyclopenta[b]furan-2-ol.

EXAMPLE 70

3.2 g. (8.6 mmol) of 3,3abeta,4,5,6,6abeta-hexahydro-4beta[3 alpha-(2-tetrahydropyranyloxy)-4-fluoro-1-trans-octenyl]5alpha-methyl-2H-cyclopenta[b]furan-2-ol in 150 ml. of hexamethylphosphoric triamide was reacted with 2.2 equivalents of Wittig reagent generated by the reaction of 7.0 g. (0.0384 mol) of sodium bis-trimethylsilyl amide with 8.4 g. (0.019 mol) of (4-carboxybutyl)-tri-phenylphosphonium bromide. After stirring for thirty minutes, the hexamethylphosphoramide was removed under high vacuum. The residue was treated with 1 N sodium hydroxide and the mixture was stirred for 2 hours at room temperature. The mixture was then extracted with ether and the water layer separated and cautiously acidified. The aqueous mixture was then extracted with ether. The ether solution dried (Na$_2$SO$_4$) and the solvent removed under reduced pressure. The residue was then chromatographed on silica gel to give 3.5 g. of 7-(3alpha-methyl-5alpha-hydroxy-2beta[3alpha-(2-tetrahydropyranyloxy)-4-fluoro-1-trans-octenyl]-1-alpha-cyclopentyl)-cis-5-heptanoic acid.

EXAMPLE 71

By the procedure of Example 70, 3,3abeta,4,5,6-,6abeta-hexahydro-4beta[3alpha(2-tetrahydropyranyloxy)-4-fluoro-4-methyl-1-trans-octenyl]-5alpha methyl-2H-cyclopenta[b]furan-2-ol is converted to 7{3alpha-methyl-5alpha-hydroxhy-2beta[3alpha-(2-tetrahydropyranyloxy)-4-fluoro-4-methyl-1-trans-octenyl]-1-alpha-cyclopentyl}-cis-5-heptenoic acid.

EXAMPLE 72

By the procedure of Example 70, 3,3abeta,4,5,6-,6abeta-hexahydro-4beta[3alpha(2-tetrahydropyranyloxy)-4,4-dimethyl-1-trans-octenyl]-5alpha methyl-2H-cyclopenta[b]furan-2-ol is converted to 7{3-alpha-methyl-5alpha-hydroxy-2beta[3alpha-(2-tetrahydropyranyloxy)-4,4-dimethyl-1-trans-octenyl]-1-alpha-cyclopentyl}-cis-5-heptenoic acid.

EXAMPLE 73

To a mixture of 6 g. of chromium trioxide and 9.5 g. of pyridine in 150 ml. of methylene chloride was added at 0° C. 4.5 g. of 7{3-alpha-methyl-5alpha-hydroxy-2beta[3 alpha-(2-tetrahydropyranyloxy)-4-fluoro-1-trans-octenyl]1-alpha-cyclopentyl}-cis-5-heptenoic acid dissolved in 50 ml. of methylene chloride. The mixture was stirred for 1 hour at room temperature and the mixture filtered thru a bed of celite. The celite was washed with methylene chloride and the combined methylene chloride solution washed with dilute hydrochloric acid to remove any remaining pyridine. The methylene chloride was then removed under reduced pressure and the residue treated with 50 ml. of 3:1 parts by volume acetic acid/water solution at 35° C. for 15 hours. The solvents were then removed under high vacuum and the residue purified by column chromatography to give 7-[3alpha-methyl-5-oxo-2beta(3alpha-hydroxy-4-fluoro-1-trans-octenyl)-1-alpha-cyclopentyl]cis-5-heptenoic acid.

EXAMPLE 74

By the procedure of Example 73, 7-{3-alpha-methyl-5-alpha-hydroxy-2beta[3alpha-(2-tetrahydropyranyloxy)-4-fluoro-4-methyl-1-trans-octenyl]1-alpha-cyclopentyl}-cis-5-heptenoic acid was converted to 7[-3-alpha-methyl-5-oxo-2beta(3alpha-hydroxy-4-fluoro-4-methyl-1-trans-octenyl)-1-alpha-cyclopentyl]cis-5-heptenoic acid.

EXAMPLE 75

By the procedure of Example 73, 7{3 alpha methyl-5-alpha-hydroxy-2beta[3alpha-(2-tetrahydropyranyloxy)-4,4-dimethyl-1-trans-octenyl]-1-alpha-cyclopentyl}-cis-5-heptenoic acid was converted to 7[3-alpha methyl-5-oxo-2beta (3alpha-hydroxy-4,4-dimethyl-1-trans-octenyl)1-alpha-cyclopentyl]cis-5-heptenoic acid.

EXAMPLE 76

A solution of 200 mg. of 7-{3alpha-methyl-5alpha-hydroxy-2beta[3alpha-(2-tetrahydropyranyloxy)-4-fluoro-1-trans-octenyl]-1-alpha-cyclopentyl}-cis-5-heptenoic acid in 5 ml. of 3:1 parts by volume acetic acid/water solution was kept at 35° C. for 15 hours. The solvent was then removed under high vacuum and the residue purified via column chromatography to give 7[3-alpha-methyl-5alpha-hydroxy-2beta(3alpha-hydroxy-4-fluoro-1-trans-octenyl)-1-alpha-cyclopentyl]cis-5-heptenoic acid.

EXAMPLE 77

By the procedure of Example 76, 7{3-alpha-methyl-5alpha-hydroxy-2beta[3alpha-(2-tetrahydropyranyloxy)-4-fluoro-4-methyl-1-trans-octenyl]-1-alpha-cyclopentyl}-cis-5-heptenoic acid was converted to 7[3-alpha-methyl-5alpha-hydroxy-2beta(3alpha-hydroxy-4-fluoro-4-methyl-1-trans-octenyl)-1-alpha-cyclopentyl]cis-5-heptenoic acid.

EXAMPLE 78

By the procedure of Example 76, 7{3-alpha methyl-5alpha-hydroxy-2beta[3alpha-(2-tetrahydropyranyloxy)-4,4-dimethyl-1-trans-octenyl]-1-alpha-cyclopentyl}-cis-5-heptenoic acid was converted to 7[3-alpha-methyl-5-alpha-hydroxy-2beta (3alpha-hydroxy-4,4-dimethyl-1-trans-octenyl)-1-alpha-cyclopentyl]-cis-5-heptenoic acid.

EXAMPLE 79

By the procedure of Example 58, dimethyl (2-oxo-3-fluoroheptyl) phosphonate was reacted with 3,3abeta,4,5,6,6abeta-hexahydro-4beta-formyl-2-oxo-2H-cyclopenta[b]furan to produce 3,3abeta,4,5,6,6abeta-hexahydro-4beta-(3-oxo-4-fluoro-1-trans-octenyl)-2-oxo-2H-cyclopenta[b]furan.

EXAMPLE 80

By the procedure of Example 58, 3,3abeta-4,5,6-abeta-hexahydro-4beta-formyl-2-oxo-2H-cyclopenta[b]furan was reacted with dimethyl (2-oxo-3-methyl-3-fluoroheptyl) phosphonate to give 3,3abeta,4,5,6-,6abeta-hexahydro-4beta (3-oxo-4-methyl-4-fluoro-1-trans-octenyl)-2-oxo-2H-cyclopenta[b]furan.

EXAMPLE 81

By the procedure of Example 58, 3,3abeta,4,5,6-,6abeta-hexahydro-4beta-formyl-2-oxo-2H-cyclopenta[b]furan was reacted with dimethyl-(2-oxo-3,3-dimethyl heptyl) phosphonate to give 3,3abeta,4,5,6-,6abeta-hexahydro-4-beta(3-oxo-4,4-dimethyl-1-trans-octenyl)-2-oxo-2H-cyclopenta[b]furan.

EXAMPLE 82

By the procedure of Example 61, 3,3abeta,4,5,6-,6abeta-hexahydro-4beta-(3-oxo-4-fluoro-1-trans-octenyl)-2-oxo-2H-cyclopenta[b]furan was reacted to give 3,3abeta,4,5,6,6abeta-hexahydro-4beta-(3-hydroxy-4-fluoro-1-trans-octenyl)-2-oxo-2H-cyclopenta[b]furan. Chromatography on silica gel in the manner of Example 61 afforded first the 3,3abeta,4,5,6,6abeta-hexahydro-4beta-(3alpha-hydroxy-4-fluoro-1-trans-octenyl)-2-oxo-2H-cyclopenta[b]furan. Also obtained by chromatography was the 3,3abeta,4,5,6,6abeta-hexahydro-4beta(3-beta-hydroxy-4-fluoro-1-trans-octenyl)-2-oxo-2H-cyclopenta[b]furan.

EXAMPLE 83

By the procedure of Example 61, 3,3abeta,4,5,6-,6abeta-hexahydro-4beta-(3-oxo-4-fluoro-4-methyl-1-trans-octenyl)-2-oxo-2H-cyclopenta[b]furan was converted to 3,3abeta,4,5,6,6abeta-hexahydro-4beta-(3alpha-hydroxy-4-fluoro-4-methyl-1-trans-octenyl)-2-oxo-2H-cyclopenta[b]furan and 3,3abeta,4,5,6,6abeta-hexahydro-4beta(3beta-hydroxy-4-fluoro-4-methyl-1-trans-octenyl)-2-oxo-2H-cyclopenta[b]furan which were separated by column chromatography in the manner of Example 61.

EXAMPLE 84

By the procedure of Example 61, 3,3abeta,4,5,6-,6abeta-hexahydro-4-beta-(3-oxo-4,4-dimethyl-1-trans-octenyl)-2-oxo-2H-cyclopenta[b]furan was converted to 3,3abeta,4,5,6,6abeta hexahydro-4-beta(3alpha-hydroxy-4,4-dimethyl-1-trans-octenyl)-2-oxo-2H-cyclopenta[b]furan and 3,3abeta,4,5,6,6abeta-hexahydro-4-beta-(3-beta-hydroxy-4,4-dimethyl-1-trans-octenyl)-2-oxo-2H-cyclopenta[b]furan which were separated by chromatography in the manner of Example 61.

EXAMPLE 85

By the procedure of Example 64, 3,3abeta-4,5,6,6abeta-hexahydro-4beta-[3alpha-hydroxy-4-fluoro-1-trans-octenyl]-2-oxo-2H-cyclopenta[b]furan was converted to 3,3abeta,4,5,6,6abeta-hexahydro-4beta[3alpha(2-tetrahydropyranyloxy)-4-fluoro-1-trans-octenyl]-2-oxo-2H-cyclopenta[b]furan.

EXAMPLE 86

By the procedure of Example 64, 3,3abeta,4,5,6-,6abeta-hexahydro-4beta-(3alpha-hydroxy-4-fluoro-4-methyl-1-trans-octenyl)-2-oxo-2H-cyclopenta[b]furan was converted to 3,3abeta,4,5,6,6abeta-hexahydro-4beta[3alpha-(2-tetrahydropyranyloxy)-4-fluoro-4-methyl-1-trans-octenyl]-2-oxo-2H-cyclopenta[b]furan.

EXAMPLE 87

By the procedure of Example 64, 3,3abeta,4,5,6-,6abeta-hexahydro-4beta-(3alpha-hydroxy-4,4-dimethyl-1-trans-octenyl)-2H-cyclopenta[b]furan-2-one is converted to 3,3abeta,4,5,6,6abeta-hexahydro-4beta-[3alpha(2-tetrahydropyranyloxy)-4,4-dimethyl-1-trans-octenyl]-2H-cyclopenta[b]furan-2-one.

EXAMPLE 88

By the procedure of Example 67, 3,3abeta,4,5,6-,6abeta-hexahydro-4beta-[3alpha(2-tetrahydropyranyloxy)-4-fluoro-1-trans-octenyl]-2-oxo-2H-cyclopenta[b]furan is converted to 3,3abeta,4,5,6-,6abeta-hexahydro-4beta[3alpha(2-tetrahydropyranyloxy)-4-fluoro-1-trans-octenyl]-2H-cyclopenta[b]furan-2-ol.

EXAMPLE 89

By the procedure of Example 67, 3,3abeta,4,5,6-,6abeta-hexahydro-4beta-[3alpha(2-tetrahydropyranyloxy)-4-fluoro-4-methyl-1-trans-octenyl]-2-oxo-2H-cyclopenta[b]furan was converted to 3,3abeta,4,5,6,6abeta-hexahydro-4beta[3alpha(2-tetrahydropyranyloxy)-4-fluoro-4-methyl-1-trans-octenyl]-2H-cyclopenta[b]furan-2-ol.

EXAMPLE 90

By the procedure of Example 67, 3,3abeta,4,5,6-,6abeta-hexahydro-4beta-[3alpha(2-tetrahydropyranyloxy)-4,4-dimethyl-1-trans-octenyl]-2-oxo-2H-cyclopenta[b]furan was converted to 3,3abeta,4,5,6-,6abeta-hexahydro-4beta[3alpha(2-tetrahydropyranyloxy)-4,4-dimethyl-1-trans-octenyl]-2H-cyclopenta[b]furan-2-ol.

EXAMPLE 91

By the procedure of Example 70, 3,3abeta,4,5,6-,6abeta-hexahydro-4beta[3alpha-(2-tetrahydropyranyloxy)-4-fluoro-1-trans-ocentyl]-2H-cyclopenta[b]furan-2-ol was converted to 7-(5alpha-hydroxy-2-beta[3-alpha-(2-tetrahydropyranyloxy)-4-fluoro-1-trans-octenyl]-1-alphacyclopentyl)-cis-5-heptenoic acid.

EXAMPLE 92

By the procedure of Example 70, 3,3abeta,4,5,6-,6abeta-hexahydro-4beta[3alpha(2-tetrahydropyranyloxy)-4-fluoro-4-methyl-1-trans-octenyl]-2H-cyclopenta[b]furan-2-ol was converted to 7{5-alpha-hydroxy-2beta[3alpha-(2-tetrahydropyranyloxy)-4-fluoro-4-methyl-1-trans-octenyl]-1-alpha-cyclopentyl}-cis-5-heptenoic acid.

EXAMPLE 93

By the procedure of Example 70, 3,3abeta,4,5,6-,6abeta-hexahydro-4beta[3alpha(2-tetrahydropyranyloxy)4,4-dimethyl-1-trans-octenyl]-2H-cyclopenta[b]furan-2-ol was converted to 7{5-alpha-hydroxy-2beta[3alpha-(2-tetrahydropyranyloxy)-4,4-dimethyl-1-trans-octenyl]-1-alpha-cyclopentyl}-cis-5-heptenoic acid.

EXAMPLE 94

By the procedure of Example 73, 7{5alpha-hydroxy-2beta[3alpha-(2-tetrahydropyranyloxy)-4-fluoro-1-trans-octenyl]-1-alpha-cyclopentyl}cis-5-heptenoic acid was converted to 7{5-oxo-2beta(3alpha-hydroxy-4-fluoro-1-trans-octenyl)-1-alpha-cyclopentyl}cis-5-heptenoic acid.

EXAMPLE 95

By the procedure of Example 73, 7{5-alpha-hydroxy-2beta[3alpha-(2-tetrahydropyranyloxy)-4-fluoro-4-methyl-1-trans-octenyl]-1-alpha-cyclopentyl}-cis-5-heptenoic acid was converted to 7[5-oxo-2beta(3alpha-hydroxy-4-fluoro-4-methyl-1-trans-octenyl)-1-alpha-cyclopentyl]cis-5-heptenoic acid.

EXAMPLE 96

By the procedure of Example 73, 7{5-alpha-hydroxy-2beta-[3alpha-(2-tetrahydropyranyloxy)-4,4-dimethyl-1-trans-octenyl]-1-alpha-cyclopentyl}-cis-5-heptenoic acid was converted to 7[5-oxo-2beta(3alpha-hydroxy-4,4-dimethyl-1-trans-octenyl)-1-alpha-cyclopentyl]cis-5-heptenoic acid.

EXAMPLE 97

A solution of 200 mg. of 7-{5alpha-hydroxy-2beta[-3alpha-(2-tetrahydropyranyloxy-4-fluoro-1-trans-octenyl]-1-alpha-cyclopentyl}-cis-5-heptenoic acid in 5 ml. of a 3:1 parts by volume acetic acid/water solution was kept at 35° C. for 15 hours. The solvent was then removed under high vacuum and the residue purified via column chromatography to give 7[5alpha-hydroxy-2beta(3alpha-hydroxy-4-fluoro-1-trans-octenyl)-1-alpha-cyclopentyl]-cis-5-heptenoic acid.

EXAMPLE 98

By the procedure of Example 73, 7{5alpha-hydroxy-2beta[3alpha-(2-tetrahydropyranyloxy)-4-fluoro-4-methyl-1-trans-octenyl]-1-alpha-cyclopentyl}cis-5-heptenoic acid was converted to 7[5-oxo-2beta-(3alpha-hydroxy-4-fluoro-4-methyl-1-trans-octenyl)-1-alpha-cyclopentyl]cis-5-heptenoic acid.

EXAMPLE 99

By the procedure of Example 73, 7{5alpha-hydroxy-2beta-[3alpha-(2-tetrahydropyranyloxy)-4,4-dimethyl-1-trans-octenyl]-1-alpha-cyclopentyl}-cis-5-heptenoic acid was converted to 7[5-oxo-2beta(3alpha-hydroxy-4,4-dimethyl-1-trans-octenyl)-1-alpha-cyclopentyl]cis-5-heptenoic acid.

EXAMPLE 100

3,3abeta,4,5,6,6abeta-hexahydro-4beta[4,4-dimethyl-3alpha(2-tetrahydropyranyloxy)-1-trans-octenyl]-5alpha methoxy methyl-2H-cyclopenta[b]furan-2-one.

A solution of 5.5 g. of 3,3abeta,4,5,6,6abeta-hexahydro-4beta[4,4-dimethyl-3alpha(2-tetrahydropyranyloxy)-1-trans-octenyl]-5alpha hydroxymethyl-2H-cyclopenta[b]furan-2-one in 10 ml. of dimethoxyethane was added dropwise to a stirred slurry of 0.34 g. of sodium hydride in 40 ml. of dimethoxyethane. After ten minutes, 2.0 g. of methyl iodide was added and the mixture was stirred for two hours. The mixture was then diluted with 100 ml. of diethyl ether and 50 ml. of hexane, washed with saturated aqueous sodium chloride solution, dried (MgSO4) and the solvent evaporated to yield 5.45 g. of crude 3,3abeta,4,5,6,6abeta-hexahydro-4beta[4,4-dimethyl-3alpha(2-tetrahydropyranyloxy)-1-trans-octenyl]-5alpha methoxymethyl-2H-cyclopenta[b]furan-2-one which was purified by dry column chromatography over silica gel.

EXAMPLE 101

3,3abeta,4,5,6,6abeta-hexahydro-4beta[4,4-dimethyl-3alpha(2-tetrahydropyranyloxy)1-trans-octenyl]5alpha methoxymethyl-2H-cyclopenta[b]furan-2-ol By the procedure of Example 2, 3,3abeta,4,5,6,6abeta-hexahydro-4beta[4,4-dimethyl-3alpha(2-tetrahydropyranyloxy)-1-trans-octenyl]5alpha methoxymethyl-2H-cyclopenta[b]furan-2-one was reduced with bis-3-methyl-2-butylborane in tetrahydrofuran to 3,3abeta,4,5,6,6abeta-hexahydro-4beta[4,4-dimethyl-3alpha(2-tetrahydropyranyloxy)-1-trans-octenyl]-5alpha methoxymethyl-2H-cyclopenta[b]furan-2-ol.

EXAMPLE 102 methyl 7-{2beta[4,4-dimethyl-3alpha(2-tetrahydropyranyloxy)-1-trans-octenyl]-3alpha methoxymethyl-5alpha hydroxy-1alpha cyclopentyl}-cis-5-heptenoate By the procedure of Example 3, 3,3abeta,4,5,6,6abeta-hexahydro-4beta[4,4-dimethyl-3alpha(2-tetrahydropyranyloxy)-1-trans-octenyl]-5alpha methoxymethyl-2H-cyclopenta[b]furan-2-ol was converted in hexamethyl phosphoramide with the Wittig reagent derived from (4-carboxybutyl)triphenylphosphonium bromide to 7-{2beta[4,4-dimethyl-3alpha(2-tetrahydropyranyloxy)1-trans-octenyl]-3alpha methoxymethyl-5alpha hydroxy-1alpha-cyclopentyl}cis-5-heptenoic acid, which when treated with 1.1 equivalent of diazomethane in ethyl ether gave methyl 7-{2beta[4,4-dimethyl-3alpha(2-tetrahydropyranyloxy)1-trans-octenyl]3alpha methoxymethyl-5alpha hydroxy-1alpha cyclopentyl}-cis-5-heptenoate.

EXAMPLE 103 methyl 7-{2beta(4,4-dimethyl-3alpha hydroxy-1-trans-octenyl)3alpha methoxymethyl-5alpha hydroxy-1alpha cyclopentyl}cis-5-heptenoate A solution of 400 mg. of 7-{2beta[4,4-dimethyl-3alpha(2-tetrahydropyranyloxy)1-trans-octenyl]-3alpha methoxymethyl-5alpha hydroxy-1alpha cyclopentyl}-cis-5-heptenoic acid in 50 ml. of a mixture of acetic acid, water and acetonitrile (2:1:4) was warmed at 37° C. for 15 hours. Evaporation of the solvent followed by purification by column chromatography over silica gel yielded 274 mg. of 7-{2beta(4,4-dimethyl-3alpha-hydroxy-1-trans-octenyl)-3alpha methoxymethyl-5alpha hydroxy-1alpha cyclopentyl}-cis-5-heptenoic acid which was converted to methyl 7-{2beta(4,4-dimethyl-3alpha-hydroxy-1-trans-octenyl)-3alpha methoxymethyl-5alpha hydroxy-1alpha cyclopentyl}-cis-5-heptenoate by reaction with etheral diazomethane.

EXAMPLE 104 methyl 7-{2beta(4,4-dimethyl-3alpha hydroxy-1-trans-octenyl)-3alpha methoxymethyl-5-oxo-1alpha cyclopentyl}-cis-5-heptenoate A solution of methyl 7-{2beta[4,4-dimethyl-3alpha(2-tetrahydropyranyloxy)-1-trans-octenyl]-3alpha methoxymethyl-5alpha hydroxy-1alpha cyclopentyl}-cis-5-heptenoate (1.0 g.) in 5 ml. of methylene chloride was mixed with a solution of 1.75 g. of pyridine and 1.1 g. of chromium trioxide in 30 ml. of methylene chloride. After thirty minutes, the mixture was diluted with 100 ml. of ethyl ether and successively washed with 0.5 M sodium hydroxide, 0.5 N sulfuric acid, and 5% sodium bicarbonate, dried (MgSO4) and the solvent evaporated to give 0.98 g. of crude methyl 7-{2beta[4,4-dimethyl-3alpha(2-tetrahydropyranyloxy)-1-trans-octenyl]-3alpha methoxymethyl-5-oxo-1alpha cyclopentyl}cis-5-heptenoate which was hydrolyzed to methyl 7-{2beta(4,4-dimethyl-3alpha hydroxy-1-trans-octenyl)-3alpha methoxymethyl-5-oxo-1alpha cyclopentyl}cis-5-heptenoate in 100 ml. of a mixture of acetic acid, water and acetonitrite (1:1:2) at 37°-40° C.

EXAMPLE 105

7-{2beta(4,4-dimethyl-3alpha hydroxy-1-trans-octenyl)-3alpha methoxymethyl-5-oxo-1alpha cyclopentyl}cis-5-heptenoic acid A solution of 66 mg. of methyl 7-{2beta(4,4-dimethyl-3alpha hydroxy-1-trans-octenyl)-3alpha methoxymethyl-5-oxo-1alpha cyclopentyl}cis-5-heptenoate in 20 ml. of methanol and 2 ml. of 6% sodium hydroxide was warmed to 37°-40° C. for 10 hours. Most of the methanol was evaporated at reduced pressure and the residue acidified to pH 3 with 0.5 N sulfuric acid, saturated with sodium chloride, and extracted with ethyl acetate. Evaporation of the dried (MgSO4) ethyl acetate extract yielded 45 mg. of 7-{2beta(4,4-dimethyl-3alpha hydroxy-1-trans-octenyl)-3alpha methoxymethyl-5-oxo- 1alpha cyclopentyl}-cis-5-heptenoic acid which was purified by column chromatography over silica gel.

EXAMPLE 106

7-[3alpha carbomethoxy-5-oxo-2beta(3beta hydroxy-1-trans-octenyl)-1alpha cyclopentyl]-cis-5-heptenoic acid By the procedure of Example 1, 3,3abeta,4,5,6,6abeta-4beta(3beta hydroxy-1trans-octenyl)-5alpha carbomethoxy-2-oxo-2H-cyclopenta[b]-furan was converted to 3,3abeta,4,5,6,6abeta-hexahydro-4beta[3beta(2-tetrahydropyranyloxy)-1-trans-octenyl]-5-alpha-carbomethoxy-2-oxo-2H-cyclopenta[b]furan; m.p. 55°-57° C., which was converted by the procedure of Example 2 to give 3,3abeta,4,5,6,6abeta-hexahydro-4beta[3beta(2-tetrahydropyranyloxy)-1-trans-octenyl]-5-alpha carbomethoxy-2H-cyclopenta[b]furan-2-ol which was converted by the procedure of Example 3 to 7-{3alpha carbomethoxy-5alpha-hydroxy-2beta[3beta(2 tetrahydropyranyloxy)-1-trans-octenyl]-1-alpha cyclopentyl}-cis-5-heptenoic acid which upon hydrolysis by the procedure of Example 7 gave 7-[3alpha carbomethoxy-5alpha hydroxy-2beta(3beta-hydroxy-1-trans-octenyl)-1-alpha cyclopentyl]-cis-5-heptenoic acid. Alternatively, oxidation by the procedure of Example 19 gave 7-{3alpha carbomethoxy-5-oxo-2beta[3beta(2-tetrahydropyranyloxy)-1-trans-octenyl]-1-alpha cyclopentyl}-cis-5-heptenoic acid which was hydrolyzed by the procedure of Example 7 to 7-[3alpha carbomethoxy-5-oxo-2beta(3beta hydroxy-1-trans-octenyl)-1alpha cyclopentyl]-cis-5-heptenoic acid.

EXAMPLE 107

By the procedures described in Examples 64, 67, 70, 73 and 76, 3,3abeta-4,5,6,6abeta-hexahydro-4beta(3beta-hydroxy-4-fluoro-1-trans-octenyl)5alpha-methyl-2-oxo-2H-cyclopenta[b]furan was converted to the following compounds:
1. 3,3abeta-4,5,6,6abeta-hexahydro-4beta[3beta(2-tetrahydropyranyloxy)-4-fluoro-1-trans-octenyl 5alpha-methyl-2-oxo-2H-cyclopenta[b]furan.
2. 3,3abeta-4,5,6,6abeta-hexahydro-4beta[3beta(2-tetrahydropyranyloxy)-4fluoro-1-trans-octenyl]5alpha-methyl-2H-cyclopenta[b]furan-2-ol.
3. 7-{3alpha-methyl-5alpha-hydroxy-2beta[3beta(2-tetrahydropyranyloxy)-4-fluoro-1-trans-octenyl]-1alpha-cyclopentyl}cis-5-heptenoic acid.
4. 7[3alpha-methyl-5-oxo-2beta(3beta-hydroxy-4-fluoro-1-trans-octenyl)1alpha-cyclopentyl]cis-5-heptenoic acid.
5. 7[3alpha-methyl-5alpha-hydroxy-2beta(3beta-hydroxy-4-fluoro-1-trans-octenyl)1alpha-cyclopentyl]cis-5-heptenoic acid.

EXAMPLE 108

A tablet was found containing the following ingredients:

| | Per Tablet |
|---|---|
| 7-[3 alpha-methyl-5-oxo-2 beta-(3 alpha-hydroxy-4-fluoro-1-trans-octenyl)-1 alpha-cyclopentyl]-cis-5-heptenoic acid | 200 mg. |
| Dicalcium Phosphate Dihydrate, Unmilled | 235 mg. |
| Corn Starch | 70 mg. |
| FD&C Yellow #5 - Aluminum Lake 25% | 2 mg. |
| Durkee Duratex* | 25 mg. |
| Calcium Stearate | 3 mg. |
| TOTAL Weight | 535 mg. |

*Hydrogenated Cotton Seed Oil (Fully Saturated).

All of the above ingredients were mixed until thoroughly blended in a suitable size container. The powder was filled into #2, two-piece, hard shell gelatin capsules to an approximate fill weight of 350 mg. using a capsulating machine.

EXAMPLE 109

A capsule was prepared by the procedure of Example 108 except that 7-[2-beta-(4,4-dimethyl-3-alpha-hydroxy-1-transoctenyl)-5-oxo-1alpha-cyclopentyl]cis-5-heptenoic acid was the active ingredient.

EXAMPLE 110

A capsule was prepared by the procedure of Example 108 except that 7-[3alpha-methyl-5-oxo-2beta-(3alpha-hydroxy-4-fluoro-1-trans-octenyl)-1-alpha-cyclopentyl]-cis-5-heptenoic acid methyl ester was the active ingredient.

EXAMPLE III

A capsule was prepared by the procedure of Example 109 except that methyl 7-[2beta-(4,4-dimethyl-3alpha-hydroxy-1-trans-octenyl)-5-oxo-1alpha-cyclopentyl]cis-5-heptenoate was the active ingredient.

EXAMPLE 112

A tablet was found containing:

| | Per Tablet |
|---|---|
| 7-[3 alpha-methyl-5-oxo-2 beta-(3 alpha-hydroxy-4-fluoro-1-trans-octenyl)-1 alpha-cyclopentyl]-cis-5-heptenoic acid | 25 mg. |
| Dicalcium Phosphate Dihydrate, Unmilled | 175 mg. |
| Corn Starch | 24 mg. |
| Magnesium Stearate | 1 mg. |
| TOTAL Weight | 225 mg. |

The 7-[3-alpha-methyl-5-oxo-2beta-(3alpha-hydroxy-4-fluoro-1-trans-octenyl)-1alpha-cyclopentyl]-cis-5-heptenoic acid and corn starch were mixed together and passed through a #00 screen in Model "J" Fitzmill with hammers forward. This premix was then mixed with dicalcium phosphate and one-half of the magnesium stearate, passed through a #1A screen in Model "J" Fitzmill with knives forward, and slugged. The slugs were passed through a #2A plate in a Model "D" Fitzmill at slow speed with knives forward, and the remaining magnesium stearate was added. The mixture was mixed and compressed.

EXAMPLE 113

A tablet was formulated in the same manner as in Example 112 except that 7-[2beta-(4,4-dimethyl-3-alpha-hydroxy-1-trans-octenyl)-5-oxo-1alpha-cyclopentyl]cis-5-heptenoic acid was the active ingredient.

EXAMPLE 114

A tablet was formulated in the same manner as in Example 112 except that 7-[3alpha-methyl-5-oxo-2beta-(3alpha-hydroxy-4-fluoro-1-trans-octenyl)-1alpha-cyclopentyl]-cis-5-heptenoic acid methyl ester was the active ingredient.

EXAMPLE 115

A tablet was formulated in the same manner as in Example 112 except that methyl 7-[2beta-(4,4-dimethyl-3alpha-hydroxy-1-trans-octenyl)-5-oxo-1alpha-cyclopentyl]-cis-5-heptenoate was the active ingredient.

We claim:

1. A composition of matter comprising a compound of the formula:

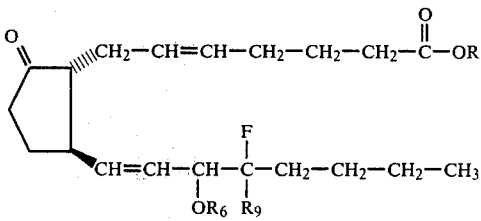

wherein R is hydrogen or lower alkyl; $R_6$ is hydrogen or lower alkanoyl, tetrahydropyranyl, benzoyl, trialkylsilyl, benzyl, benzhydryl, trityl; and $R_9$ is hydrogen or lower alkyl or enantiomers or racemates thereof.

2. The composition of claim 1 wherein $R_6$ is hydrogen.

3. The composition of claim 2 wherein said compound is 7[5-oxo-2beta(3-alpha-hydroxy-4-fluoro-4-methyl-1-trans-octenyl)-1-alpha-cyclopentyl]-cis-5-heptenoic acid.

4. The composition of claim 2 wherein said compound is 7[5-oxo-2beta(3alpha-hydroxy-4-fluoro-1-trans-octenyl)-1-alpha-cyclopentyl]-cis-5-heptenoic acid.

* * * * *